(12) United States Patent
Levin et al.

(10) Patent No.: US 9,163,067 B2
(45) Date of Patent: Oct. 20, 2015

(54) HIV-1 INTEGRASE DERIVED STIMULATORY PEPTIDES INTERFERING WITH INTEGRASE—REV PROTEIN BINDING

(75) Inventors: Aviad Levin, Holon (IL); Zvi Hayouka, Jerusalem (IL); Assaf Friedler, Mevaseret Zion (IL); Abraham Loyter, Jerusalem (IL)

(73) Assignee: Yissum Research Development Company of The Hebrew University of Jerusalem Ltd, Jerusalem (IL)

( * ) Notice: Subject to any disclaimer, the term of this patent is extended or adjusted under 35 U.S.C. 154(b) by 266 days.

(21) Appl. No.: 13/122,548

(22) PCT Filed: Oct. 1, 2009

(86) PCT No.: PCT/IL2009/000947
§ 371 (c)(1),
(2), (4) Date: Jun. 27, 2011

(87) PCT Pub. No.: WO2010/041241
PCT Pub. Date: Apr. 15, 2010

(65) Prior Publication Data
US 2011/0257082 A1    Oct. 20, 2011

Related U.S. Application Data

(60) Provisional application No. 61/103,036, filed on Oct. 6, 2008, provisional application No. 61/225,028, filed on Jul. 13, 2009.

(51) Int. Cl.
| | | |
|---|---|---|
| A61K 38/00 | (2006.01) | |
| A01N 37/18 | (2006.01) | |
| A61P 31/18 | (2006.01) | |
| A61K 38/10 | (2006.01) | |
| A61K 38/16 | (2006.01) | |
| C07K 14/005 | (2006.01) | |

(52) U.S. Cl.
CPC ............ *C07K 14/005* (2013.01); *A61K 38/162* (2013.01); *C07K 2319/10* (2013.01); *C12N 2740/16222* (2013.01)

(58) Field of Classification Search
None
See application file for complete search history.

(56) References Cited

U.S. PATENT DOCUMENTS

| | | | |
|---|---|---|---|
| 5,019,510 A * | 5/1991 | Wain-Hobson et al. ... | 435/235.1 |
| 2002/0119127 A1 | 8/2002 | Sette | |
| 2005/0271676 A1 | 12/2005 | Sette | |
| 2006/0257865 A1 | 11/2006 | Mallal | |
| 2007/0203325 A1 | 8/2007 | Yao | |
| 2007/0248584 A1 | 10/2007 | Kent | |
| 2008/0131451 A1 | 6/2008 | Tanzi | |

FOREIGN PATENT DOCUMENTS

| | | |
|---|---|---|
| EP | 2 003 120 | * 12/2008 |
| WO | 95/33765 | 12/1995 |
| WO | 98/32456 A1 | 7/1998 |
| WO | 99/58658 A1 | 11/1999 |
| WO | 01/24810 A1 | 4/2001 |
| WO | WO 01/24810 | * 4/2001 |
| WO | 02/094313 A1 | 11/2002 |
| WO | 03/035097 A1 | 5/2003 |
| WO | 03/040165 A1 | 5/2003 |
| WO | 2004/031210 A1 | 4/2004 |
| WO | 2004/108753 A1 | 12/2004 |
| WO | WO 2004/108753 | * 12/2004 |
| WO | 2005/033265 A1 | 4/2005 |
| WO | 2008/053478 A1 | 5/2008 |
| WO | 2008/068765 A1 | 6/2008 |
| WO | 2008/109059 A1 | 9/2008 |

OTHER PUBLICATIONS

Dwibhashyam et al, Strategies for Enhanced Drug Delivery to the Central Nervous System, Indian J Pharm Sci. Mar.-Apr. 2008; 70(2): 145-153.*
Dwibhashyam et al, Strategies for Enhanced Drug Delivery to the Central Nervous System, Indian J Pharm Sci. Mar.-Apr. 2000;70(2): 145-153.*
Lindgren et al, Cell-penetrating peptides, Trends Pharmacol Sci, Mar. 2000;21(3):99-103.*
Noever, Naturally Occurring Protease Inhibitors Potent against the Human Immunodeficiency Virus, Biochemical and Biophysical Research Communications 227, 125-130 (1996).*
Sampathkumar et al, The frequencies of naturally occurring protease inhibitor resistance mutations in HIV proviral sequences of drug naïve sex workers in Nairobi, Kenya and their correlation with host immune response driven positively selected mutations in HIV-1, BMC Infectious Diseases 2014, 14(Suppl 3):O2.*
Armon-Omer, Ayelet et al., "Correlation between shiftide activity and HIV-1 integrase inhibition by a peptide selected from a combinatorial library", J Mol Biol, 376(4):971-982 Epub Dec. 5, 2007 (2008).
Bukrinsky, Michael I. et al., "Association of integrase, matrix, and reverse transcriptase antigens of human immunodeficiency virus type 1 with viral nucleic acids following acute infection", Proc Natl Acad Sci USA, 90(13):6125-6129 (1993).

(Continued)

*Primary Examiner* — Karlheinz R Skowronek
*Assistant Examiner* — Sergio Coffa
(74) *Attorney, Agent, or Firm* — Rodney J. Fuller; Booth Udall Fuller, PLC

(57) ABSTRACT

Isolated peptides comprising sequences derived from the protein integrase of HIV-1, as well as their analogs, mixtures, conjugates with permeability enhancing moieties, and pharmaceutical compositions are disclosed. The peptides and compositions are capable of selectively killing HIV-1 infected cells and are used in treatment of HIV infection and AIDS.

6 Claims, 18 Drawing Sheets

(56) References Cited

OTHER PUBLICATIONS

Craigie, Robert et al., "A rapid in vitro assay for HIV DNA integration". Nucleic Acids Res 19(10):2729-2734 (1991).
De Soultraitet, V. Richard et al., "Peptides as new inhibitors of HIV-1 reverse transcriptase and integrase", Curr Med Chem, 10(18):1765-1778 (2003).
Derdeyn, Cynthia A. et al., "Sensitivity of human immunodeficiency virus type 1 to the fusion inhibitor T-20 is modulated by coreceptor specificity defined by the V3 loop of gp120", J Virol, 74(18):8358-8367 (2000).
Desjobert, Cecile et al., "Identification by phage display selection of a short peptide able to inhibit only the strand transfer reaction catalyzed by human immunodeficiency virus type 1 integrase", Biochemistry 43(41):13097-13105 (2004).
Fineberg, Konstantin et al., "Inhibition of nuclear import mediated by the Rev-arginine rich motif by RNA molecules", Biochemistry, 42(9):2625-2633 (2003).
Guiot, Elvire et al., "Relationship between the oligomeric status of HIV-1 integrase on DNA and enzymatic activity", J Biol Chem, 281(32):22707-22719 Epub Jun. 13, 2006 /.
Gummuluru, Suryaram et al., "An in vitro rapid-turnover assay for human immunodeficiency virus type 1 replication selects for cell-to-cell spread of virus", J Virol, 74(23):10882-10891 (2000).
Hayouka, Zvi et al., "Inhibiting HIV-1 integrase by shifting its oligomerization equilibrium", Proc Natl Acad Sci U S A, 104(20):8316-8321 Epub May 8, 2006 (2007).
Hwang, Young et al., "Rapid microtiter assays for poxvirus topoisomerase, mammalian type IB topoisomerase and HIV-1 integrase: application to inhibitor isolation", Nucleic Acids Res, 28(24):4884-4892 (2000).
Jenkins, Timothy M. et al., "A soluble active mutant of HIV-1 integrase: involvement of both the core and carboxyl-terminal domains in multimerization", J Biol Chem, 271(13):7712-7718 (1996).
Kimpton, Jaculyn and Emerman, Michael "Detection of replication-competent and pseudotyped human immunodeficiency virus with a sensitive cell line on the basis of activation of an integrated beta-galactosidase gene", J Virol, 66(4):2232-2239 (1992).
Levin, Aviad et al., "Peptides derived from HIV-1 integrase that bind Rev stimulate viral genome integration", PLoS One, 4(1):e4155 (2009).
Levin, Aviad et al., "Specific eradication of HIV-1 from infected cultured cells", AIDS Res Ther, 7:31 (2010).
Li, Hui-Yuan et al., "Sequence-based design and discovery of peptide inhibitors of HIV-1 integrase: insight into the binding mode of the enzyme", J Med Chem, 49(15):4477-4486 (2006).
Maroun, Richard G. et al., "Peptide inhibitors of HIV-1 integrase dissociate the enzyme oligomers", Biochemistry, 40(46):13840-13848 (2001).
Oz Gleenberg, Iris et al., "Peptides derived from the reverse transcriptase of human immunodeficiency virus type 1 as novel inhibitors of the viral integrase", J Biol Chem, 280(23):21987-21996 Epub Mar. 23, 2005.
Puras Lutzke, Ramon A. et al., "Identification of a hexapeptide inhibitor of the human immunodeficiency virus integrase protein by using a combinatorial chemical library", Proc Natl Acad Sci USA, 92(25):11456-11460 (1995).
Ratner, L. et al., "Complete nucleotide sequence of the AIDS virus, HTLV-III", Nature, 313(6000):277-284 (1985).
Rosenbluh, Joseph et al., "Interaction between HIV-1 Rev and integrase proteins: a basis for the development of anti-HIV peptides", J Biol Chem, 282(21):15743-15753 Epub Apr. 2, 2007.
Yamamoto, Norio et al., "Analysis of human immunodeficiency virus type 1 integration by using a specific, sensitive and quantitative assay based on real-time polymerase chain reaction", Virus Genes, 32(1):105-113 (2006).
Zhao, Lei et al., "Interfacial peptide inhibitors of HIV-1 integrase activity and dimerization", Bioorg Med Chem Lett, 13(6):1175-1177 (2003).
International Search Report and written opinion of PCT/IL2009/000947 dated Oct. 28, 2010 (25 pages).
Field et al., (2002) Polyunsaturated fatty acids decrease the expression of sterol regulatory element-binding protein-1 in CaCo-2 cells: effect on fatty acid synthesis and triacylglycerol transport. Biochem J 368(pt 3): 855-864.
Kohler et al., (1989) Enhancement of transformation rates in higher plants by low-dose irradiation: Are DNA repair systems involved in the incorporation of exogenous DNA into the plant genome? Plant Mol Biol 12(2): 189-199.
Melchior et al., (1993) Inhibition of nuclear protein import by nonhydrolyzable analogues of GTP and identification of the small GTPase Ran/TC4 as an essential transport factor. J Cell Biol 123(6 pt 2): 1649-1659.
Oz Gleenberg et al., (2007) Inhibition of human immunodeficiency virus type-1 reverse transcriptase by a novel peptide derived from the viral integrase. Arch Biochem Biophys 458(2): 202-212.
Anonymous: "Poster Session a of ILANIT/FISEB 2008", Mar. 16, 2008, pp. 49-110, XP055170826. Retrieved from the Internet: URL: http://www.weizmann.ac.il/conferences/FISEB2008.xx/new_pages/other/abstracts_pdf/Scientific_Program_Poster_Presentations.pdf (Retrieved on Feb. 19, 2015).
Levin et al., (2008) Regulation of the HIV-1 integrase activity by the viral rev protein: the effect of cell permeable peptides derived from the integrase and rev proteins—poster session A, PA-326. ILANIT/FISEB 2008, Jan. 29, 2008, pp. 1-1, XP055170823. Retrieved from the Internet: URL: http://www.weizmann.ac.il/conferences/FISEB08.xx/new_pages/other/abstracts_pdf/Posters%20A.pdf (retrieved on Feb. 19, 2015).
Mellors et al., (1996) Prognosis in HIV-1 infection predicted by the quantity of virus in plasma. Science 272(5265): 1167-70.

* cited by examiner

```
                          SEQUENCE LISTING

<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 1

His Leu Lys Thr Ala Val Gln Met Ala Val Phe Ile His Asn Phe Lys
1               5                   10                  15

Arg

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Gly Ser Asn Phe Thr Ser Thr Thr Val Lys Ala
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 3

Thr Ala Val Gln Met Ala Val Phe Ile His Asn Phe Lys Arg Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Thr His Leu Glu Gly Lys Ile Ile Leu Val Ala Val His Val Ala
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Trp Gly Ser Asn Phe Thr Ser Thr Thr Val Lys Ala
1               5                   10

<210> SEQ ID NO 6
<211> LENGTH: 16
```

```
<212> TYPE: PRT
<213> ORGANISM: Artificial Sequence
<220> FEATURE:
<223> OTHER INFORMATION: Synthetic Peptide

<400> SEQUENCE: 6

Trp Thr Ala Val Gln Met Ala Val Phe Ile His Asn Phe Lys Arg Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 7

Trp Thr His Leu Glu Gly Lys Ile Ile Leu Val Ala Val His Val Ala
1               5                   10                  15

<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 8

Arg Cys Trp Leu Gln Met Trp Gln Glu Ser Phe Asp Leu Val Ala Met
1               5                   10                  15

Leu Gly Asp Thr
            20
```

HIV-1 INTEGRASE DERIVED STIMULATORY PEPTIDES INTERFERING WITH INTEGRASE—REV PROTEIN BINDING

RELATED APPLICATION DATA

This application is the U.S. National Stage of PCT/IL2009/000947, filed Oct. 1, 2009, which claims the benefit of U.S. Provisional Patent Application Nos. 61/103,036, filed Oct. 6, 2008 and 61/225,028, filed Jul. 13, 2009, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,373 byte ASCII (text) file named "Seq_List" created on Apr. 4, 2011.

FIELD OF THE INVENTION

The present invention relates to bioactive peptides derived from the protein integrase (IN) of human immunodeficiency virus type 1 (HIV-1), and to compositions comprising these peptides, useful in treatment of HIV-1 infection.

BACKGROUND OF THE INVENTION

The human immunodeficiency virus type 1 (HIV-1) integrase protein (IN) is a 32-kDa protein contained in the virus and following infection, it is released into the cytoplasm of infected cells. After virus-cell fusion, a process which promotes entry of the HIV-1 genome into an infected cell, the viral RNA is converted into double stranded DNA (cDNA). The viral DNA which becomes part of the preintegration complex (PIC) is eventually integrated into the host chromosomal DNA (Bukrinsky et al., 1993, Proc Natl Acad Sci USA 90, 6125-6129). Within the cytoplasm, IN catalyzes the first step of the integration process, namely the 3'-end processing in which an IN dimer removes a pGT dinucleotide from the 3' end of each viral long terminal repeat (LTR) (Guiot et al., 2006, J Biol Chem 281, 22707-22719). Following nuclear import of the PIC, the host chromosomal DNA becomes accessible to the viral cDNA and the second step of the integration process, namely the strand-transfer step that is catalyzed by an IN tetramer takes place. This ordered sequence of events, centered on integration, is mandatory for HIV replication. Although each HIV-1 infected cell contains several copies of the viral genome, only a limited number of integration events per cell, mostly one or two, have been observed.

Due to its central role in HIV replication, the IN protein is an attractive target for antiviral therapy. Moreover, probably no cellular counterpart of IN exists in human cells and therefore, IN inhibitors will not interfere with normal cellular processes. However, only a few IN inhibitors have been identified to date.

Specific domains within viral proteins are responsible for their interaction with host-cell receptors and with other viral and cellular proteins enabling the completion of the viral propagation cycle within the host cell. Peptides derived from these binding domains may interfere with virus-host and virus-virus protein interactions and as such are candidates for therapeutic agents. Using this approach, short peptides that inhibit IN enzymatic activity were obtained following analysis of the interaction between two of the HIV-1 proteins, reverse transcriptase (RT) and IN. Screening a complete library of RT-derived peptides demonstrated that two domains of about 20 amino acids mediate this interaction. Peptides bearing these amino acid sequences blocked IN enzymatic activities in vitro (Oz et al., 2005, J Biol Chem 280, 21987-21996).

A limited number of IN inhibitory peptides have already been described. Using a combinatorial peptide library, a hexapeptide was selected that inhibited the 3'-processing and integration activity of IN (Puras et al., 1995, Proc Natl Acad Sci USA 92, 11456-11460). Based on the observation that this peptide also inhibited the IN from HIV-2, FIV, and MLV, it was suggested that a conserved region around the catalytic domain of IN is being targeted. An IN inhibitory peptide was also selected using a phage-display library (Desjobert et al, 2004, Biochemistry 43, 13097-13105). IN-derived peptides that interfered with its oligomerization also blocked its enzymatic activity (Maroun et al., 2001, Biochemistry 40, 13840-13848). Several other inhibitory peptides have been described in the last few years. Other studies described IN inhibitory peptides with anti-HIV-1 activity in some cell types (de Soultrait et al., 2003, Curr Med Chem 10, 1765-1778).

WO 2008/053478 describes IN inhibitory peptides derived from LEDGF/p75 protein. WO 2008/068765 discloses peptides comprising a fragment of the HIV-1 Rev protein which inhibit IN activity and virus replication. It was shown that the HIV-1 IN and Rev proteins can interact with each other intracellularly (Rosenbluh et al., 2007, J Biol Chem 282, 15743-15753), and speculated that the limited number of integration events observed in HIV-infected cells may result from regulated inhibition of IN enzymatic activity by the viral Rev protein. Zhao et al., 2003 (Bioorg Med Chem Lett 13, 1175-1177), discloses the peptide HLKTAVQMAVFIHNFKR (SEQ ID NO:1) corresponding to amino acid residues 171-187 of the IN, which block the protein's activity.

There is an unmet need for novel and improved compositions against HIV-1 infection, in a manner that is effective and specific to infected cells and safe to healthy cells, thereby reducing the side effects associated with known anti HIV medications.

SUMMARY OF THE INVENTION

The present invention provides molecules and compositions comprising specific peptides derived from the HIV-1 protein integrase (IN), and mixtures of such peptides, for selective killing of HIV-1 infected cells. These molecules, alone, in mixtures, or in combination with other anti HIV-1 agent, are useful in treatment of HIV-1 infection and AIDS. Surprisingly, compositions comprising specific combinations of peptides are able to completely eradicate the virus from infected cells.

Without wishing to be bound to any theory, it is thought that the peptides and combinations thereof are capable of destroying HIV-1 infected cells by inducing multiple integrations of the viral cDNA into the host chromosomal DNA.

The present invention provides, according to one aspect a pharmaceutical composition comprising at least two peptides of 8-25 amino acids, or analogs, derivatives or mimetics thereof, each peptide comprising a sequence of at least 6 amino acids derived from human HIV-1 integrase (IN) protein, wherein the two peptides are derived from two different IN regions selected from the group consisting of: residues 118-128 (GSNFTSTTVKA SEQ ID NO:2), residues 174-188 (TAVQMAVFIHNFKRK SEQ ID NO:3); and residues 66-80 (THLEGKIILVAVHVA SEQ ID NO:4), further comprising a pharmaceutically acceptable carrier or diluent. According to some embodiments the pharmaceutical composition is capable of causing complete eradication of the virus.

According to some embodiments at least one of the peptides comprises a sequence selected from the group consisting of: GSNFTSTTVKA (SEQ ID NO:2); TAVQMAVFIHNFKRK (SEQ ID NO:3); THLEGKIILVAVHVA (SEQ ID NO:4).

According to further embodiments, the pharmaceutical composition comprises at least one peptide selected from the group consisting of: GSNFTSTTVKA (SEQ ID NO:2); TAVQMAVFIHNFKRK (SEQ ID NO:3); THLEGKIILVAVHVA (SEQ ID NO:4); WGSNFTSTTVKA (SEQ ID NO:5); WTAVQMAVFIHNFKRK (SEQ ID NO:6); WTHLEGKIILVAVHVA (SEQ ID NO:7).

According to yet other embodiments at least one of the peptides contained in the pharmaceutical composition according to the invention further comprises a permeability-enhancing moiety.

According to some embodiments permeability-enhancing moiety comprises at least one aromatic amino acid residue. According to some specific embodiments the aromatic residue is Tryptophan (Trp) while according to other embodiments the permeability-enhancing moiety is connected to the N-terminus of the peptide.

According to some embodiments the pharmaceutical composition comprises at least one peptide selected from the group consisting of: WGSNFTSTTVKA (SEQ ID NO:5); WTAVQMAVFIHNFKRK (SEQ ID NO:6); and WTHLEGKIILVAVHVA (SEQ ID NO:7).

According to certain embodiments, the pharmaceutical further comprises other anti HIV-1 agent.

According to some embodiments the other anti HIV-1 agent is a protease inhibitor or a reverse transcriptase (RT) inhibitor.

According to some specific embodiments the other anti HIV-1 agent is selected from the group consisting of: atazanavir (ATV), amprenavir, fosamprenavir (APV), tipranavir (TPV), indinavir, saquinavir, lopinavir/ritonavir, prezista, nelfinavir (NFV) and azidothymidine (AZT). According to more specific embodiments the other anti HIV-1 agent is azidothymidine (AZT) or Ro 31-8959 (Saquinavir).

According to a specific embodiment a pharmaceutical composition is provided comprising three peptides of 8-25 amino acids, wherein one peptide comprising a sequence of at least 6 amino acids derived from residues 118-128 (GSNFTSTTVKA SEQ ID NO:2) of HIV-1 IN; one peptide comprising a sequence of at least 6 amino acids derived from residues 174-188 (TAVQMAVFIHNFKRK SEQ ID NO:3) of human HIV-1 IN; and one peptide comprising a sequence of at least 6 amino acids derived from residues 66-80 (THLEGKIILVAVHVA SEQ ID NO:4) of human HIV-1.

According to another specific embodiment a pharmaceutical composition is provided comprising three peptides of 8-25 amino acids, wherein one peptide comprising a sequence of at least 6 amino acids derived from residues 118-128 (GSNFTSTTVKA SEQ ID NO:2) of HIV-1 IN; one peptide comprising a sequence of at least 6 amino acids derived from residues 174-188 (TAVQMAVFIHNFKRK SEQ ID NO:3) of human HIV-1 IN; and one peptide comprising a sequence of at least 6 amino acids derived from residues 66-80 (THLEGKIILVAVHVA SEQ ID NO:4) of human HIV-1, further comprising a protease inhibitor.

The present invention provides according to another embodiment use of a pharmaceutical composition comprising at least two peptides of 8-25 amino acids, or analogs, derivatives or mimetics thereof, each peptide comprising a sequence of at least 6 amino acids derived from human HIV-1 integrase (IN) protein, wherein the two peptides are derived from two different IN regions selected from the group consisting of: residues 118-128 (GSNFTSTTVKA SEQ ID NO:2), residues 174-188 (TAVQMAVFIHNFKRK SEQ ID NO:3); and residues 66-80 (THLEGKIILVAVHVA SEQ ID NO:4), for treating HIV-1 infection and AIDS.

According you yet another aspect, the present invention provides use of a pharmaceutical composition comprising at least two peptides of 8-25 amino acids, or analogs, derivatives or mimetics thereof, each peptide comprising a sequence of at least 6 amino acids derived from human HIV-1 integrase (IN) protein, wherein the two peptides are derived from two different IN regions selected from the group consisting of: residues 118-128 (GSNFTSTTVKA SEQ ID NO:2), residues 174-188 (TAVQMAVFIHNFKRK SEQ ID NO:3); and residues 66-80 (THLEGKIILVAVHVA SEQ ID NO:4), for the preparation of a therapeutic medicament for treatment of HIV-1 infection and AIDS.

The invention further relates to a method for treatment of HIV-1 infection or AIDS, said method comprises administering to a subject in need thereof a therapeutically effective amount of a pharmaceutical composition according to the invention. The pharmaceutical composition according to the invention is administered alone, together with other anti HIV-1 compositions or as part of the treatment regimen comprising anti HIV-1 compositions.

The present invention thus provides a method for selective killing of HIV-1 infected cells comprising contacting the cells with a composition comprising at least two peptides of 8-25 amino acids, or analogs, derivatives or mimetics thereof, each peptide comprising a sequence of at least 6 amino acids derived from human HIV-1 integrase (IN) protein, wherein the two peptides are derived from two different IN regions selected from the group consisting of: residues 118-128 (GSNFTSTTVKA SEQ ID NO:2), residues 174-188 (TAVQMAVFIHNFKRK SEQ ID NO:3); and residues 66-80 (THLEGKIILVAVHVA SEQ ID NO:4).

According to some embodiments, the method comprises contacting the cells with a composition comprising at least one peptide selected from the group consisting of: GSNFTSTTVKA (SEQ ID NO:2); TAVQMAVFIHNFKRK (SEQ ID NO:3); THLEGKIILVAVHVA (SEQ ID NO:4); WGSNFTSTTVKA (SEQ ID NO:5); WTAVQMAVFIHNFKRK (SEQ ID NO:6); WTHLEGKIILVAVHVA (SEQ ID NO:7).

According to additional embodiments, the composition further comprises other HIV-1 inhibitor.

The present invention provides according to another aspect a method for treatment of HIV-1 infection or AIDS, comprising administering to a subject in need thereof a therapeutically effective amount of a pharmaceutical composition comprising at least two peptides of 8-25 amino acids, or analogs, derivatives or mimetics thereof, each peptide comprising a sequence of at least 6 amino acids derived from human HIV-1 integrase (IN) protein, wherein the two peptides are derived from two different IN regions selected from the group consisting of: residues 118-128 (GSNFTSTTVKA SEQ ID NO:2), residues 174-188 (TAVQMAVFIHNFKRK SEQ ID NO:3); and residues 66-80 (THLEGKIILVAVHVA SEQ ID NO:4).

According to several embodiments, the pharmaceutical composition administered further comprises other anti HIV-1 agent.

Peptides, derivatives, analogs, peptidomimetics and pharmaceutical compositions according to the invention may be administered to the subject in need thereof by any suitable route of administration, including, but not limited to parenterally, orally, topically, or transdermally.

Yet, another aspect of the present invention relates to gene transfer and gene therapy. According to this aspect a method for enhancing retrovirus-induced gene transfer is provided comprising contacting cells with at least two synthetic or recombinant peptides of 8-25 amino acids, or analogs, derivatives or mimetics thereof, each peptide comprising a sequence of at least 6 amino acids derived from human HIV-1 integrase (IN) protein, wherein the two peptides are derived from two different IN regions selected from the group (TAVQMAVFIHNFKRK SEQ ID NO:3); and residues 66-80 (THLEGKIILVAVHVA SEQ ID NO:4).

According to some embodiments, the method for gene transfer is performed in-vitro.

According to some specific embodiments, the method of gene transfer comprises contacting the cells with at least one peptide comprising a sequence selected from the group consisting of: GSNFTSTTVKA (SEQ ID NO:2); TAVQMAVFIHNFKRK (SEQ ID NO:3); and THLEGKIILVAVHVA (SEQ ID NO:4).

The present invention provides, according to another aspect, a peptide of 8-25 amino acids comprising a sequence of at least 6 amino acids derived from an HIV-1 IN region selected from the group consisting of: residues 118-128 (GSNFTSTTVKA SEQ ID NO:2); residues 174-188 (TAVQMAVFIHNFKRK SEQ ID NO:3); and residues 66-80 (THLEGKIILVAVHVA SEQ ID NO:4), further comprising a permeability enhancing moiety.

According to some embodiments, the peptide comprises a sequence selected from the group consisting of: GSNFTSTTVKA (SEQ ID NO:2); TAVQMAVFIHNFKRK (SEQ ID NO:3); and THLEGKIILVAVHVA (SEQ ID NO:4).

According to some embodiments, the permeability-enhancing moiety comprises at least one aromatic amino acid residue. According to yet other embodiments the permeability-enhancing moiety is connected to the N-terminus of the peptide.

According to some specific embodiments the aromatic residue is Tryptophan (Trp), connected to the N-terminus of the peptide.

According to specific embodiments, the peptide comprises a sequence selected from the group consisting of: WGSNFTSTTVKA (SEQ ID NO:5); WTAVQMAVFIHNFKRK (SEQ ID NO:6); and WTHLEGKIILVAVHVA (SEQ ID NO:7).

Another aspect of the present invention provides use of a peptide of 8-25 amino acids comprising a sequence of at least 6 amino acids derived from an HIV-1 IN region selected from the group consisting of: residues 118-128 (GSNFTSTTVKA SEQ ID NO:2); residues 174-188 (TAVQMAVFIHNFKRK SEQ ID NO:3); and residues 66-80 (THLEGKIILVAVHVA SEQ ID NO:4), further comprising a permeability enhancing moiety, for preparation of a medicament for treatment of HIV-1 infection and AIDS.

Pharmaceutical compositions comprising a peptide of 8-25 amino acids comprising a sequence of at least 6 amino acids derived from an HIV-1 IN region selected from the group consisting of: residues 118-128 (GSNFTSTTVKA SEQ ID NO:2); residues 174-188 (TAVQMAVFIHNFKRK SEQ ID NO:3); and residues 66-80 (THLEGKIILVAVHVA SEQ ID NO:4), further comprising a permeability enhancing moiety, are also within the scope of the present invention.

According to some embodiments, the pharmaceutical composition further comprises other anti HIV-1 agent. According to several specific embodiments the other anti HIV-1 agent is a protease inhibitor or a reverse transcriptase (RT) inhibitor. According to other embodiments the other anti HIV-1 agent is selected from the group consisting of: atazanavir (ATV), amprenavir, fosamprenavir (APV), tipranavir (TPV), indinavir, saquinavir, lopinavir/ritonavir, prezista, nelfinavir (NFV), and azidothymidine (AZT).

According to other embodiments, the pharmaceutical composition comprises at least two peptides.

Use of a pharmaceutical composition comprising a peptide of 8-25 amino acids comprising a sequence of at least 6 amino acids derived from an HIV-1 IN region selected from the group consisting of: residues 118-128 (GSNFTSTTVKA SEQ ID NO:2); residues 174-188 (TAVQMAVFIHNFKRK SEQ ID NO:3); and residues 66-80 (THLEGKIILVAVHVA SEQ ID NO:4), further comprising a permeability enhancing moiety, for treating HIV-1 infection and AIDS is provided according to yet another aspect of the present invention According to some embodiments the amino terminus of the peptide, analog, derivative or mimetic disclosed in the invention or contained in a pharmaceutical composition of the invention, is modified, e.g., it may be acylated. According to additional embodiments the carboxy terminus is modified, e.g., it may be amidated, reduced or esterified.

A permeability-enhancing moiety according to the present invention is preferably connected covalently to the peptide sequence via a direct bond or via a linker, to form a peptide conjugate. The permeability-enhancing moiety may be connected to any position in the peptide moiety, directly or through a spacer, preferably to the amino terminus of the peptide.

According to a specific embodiment the permeability enhancing moiety is a fatty acid.

Any moiety known in the art to facilitate actively or passively or enhance permeability of the compound into cells may be used for conjugation with the peptide core according to the present invention. Non-limitative examples include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides. According to a preferred embodiment, the hydrophobic moiety is a lipid moiety or an amino acid moiety.

Cyclic versions of the peptides disclosed herein and contained in pharmaceutical compositions according to the invention are also within the scope of the present invention.

According to another aspect, the present invention provides IN stimulating peptides and peptide conjugates comprising peptidomimetic compounds of a sequence derived from HIV-1 IN protein, having further improved pharmacokinetics properties such as stability and cell permeability. Non limiting examples of such compounds include N-alkylation of selected residues, side-chain modifications of selected residues, inclusion of non-natural amino acids, use of carbamate, urea, sulfonamide and hydrazine for peptide bond replacement, and incorporation of non-peptide moieties including but not limited to piperidine, piperazine and pyrrolidine, through a peptide or non-peptide bond. Modified bonds between amino acid residues in peptidomimetics according to the present invention may be selected from the group consisting of: an amide, urea, carbamate, hydrazine and sulfonamide bond. Unless explicitly stated otherwise the bonds between the amino acid residues are all amide bonds.

According to another aspect of the present invention, the IN-derived peptides, analogs, derivatives and mimetics are used as lead compounds for designing, testing and selecting small molecules as anti-HIV-1 compositions.

Mixtures comprising at least two different IN-derived peptides are also within the scope of the present invention.

In another aspect, the invention comprises nucleic acids encoding those peptides of the invention which consist of natural amino acids.

According to some specific embodiments, a polynucleotide encoding a peptide sequence selected from the group consisting of GSNFTSTTVKA (SEQ ID NO:2); TAVQMAVFIHNFKRK (SEQ ID NO:3); THLEGKIILVAVHVA (SEQ ID NO:4); WGSNFTSTTVKA (SEQ ID NO:5); WTAVQMAVFIHNFKRK (SEQ ID NO:6); WTHLEGKIILVAVHVA (SEQ ID NO:7), is provided.

According to additional aspects the invention provides expression vectors and host cells comprising nucleic acid sequences encoding those peptides of the invention consisting of natural amino acids.

It is to be explicitly understood that previously known peptides are excluded from the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
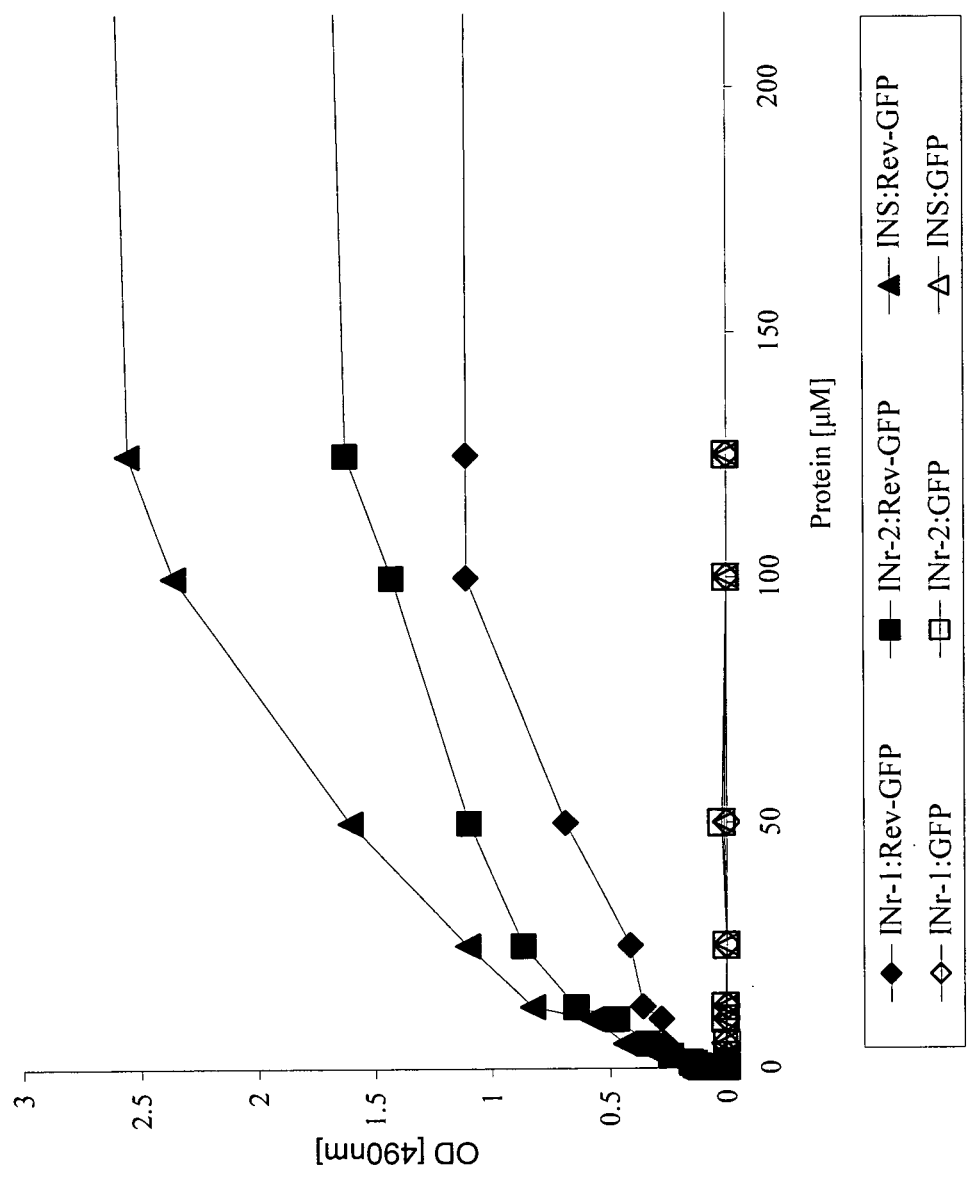
FIGS. 1A-1D depict in-vitro assay results demonstrating that the peptide INS interacts with Rev-GFP and Rev-derived peptides, and promotes dissociation of Rev-IN complexes: (A) Rev-GFP or GFP binding to ELISA plates coated with the peptides; (B) Peptide's binding to Rev-IN complex on ELISA plates, at the designated Rev-GFP:peptide ratio; (C) Rev 13-23 and Rev 53-67 (conjugated to biotinylated-BSA) binding to the peptide INS coated on ELISA plates; (D) Rev 13-23 and Rev 53-67 (conjugated to biotinylated-BSA) binding to peptides INr-1 or INr-2 coated on ELISA plates.

It is now demonstrated for the first time that the inhibitory effect on HIV-1 integrase activity, exerted by the Rev 13-23 and Rev 53-67 peptides, can be abrogated by several IN-derived peptides due to displacement of the inhibitory molecules.

The present invention is based on the finding that three peptides, designated INr-1 (SEQ ID NO:4), INr-2 (SEQ ID NO:2), and INS (SEQ ID NO:3), derived from the HIV-1 protein integrase (IN), were found to stimulate integration of the viral cDNA into host chromosomal DNA and selectively kill HIV infected cells. These peptides are derived from different regions of the IN protein. The peptides INR-1 and INR-2 abrogate the inhibitory effect of Rev while the peptide designated INS significantly stimulated the enzymatic activity of the HIV-1 IN even in the absence of the inhibitory Rev peptide. Without wishing to be bound to any theory of mechanism of action, the results indicate, based on experiments of one cycle of virus infection (FIG. 8) that cell killing is due to stimulation of integration of the viral DNA. INS and the INr-1 and 2 peptides, which have been found to be cell-permeable, stimulated integration of the HIV-1 cDNA into host chromosomal DNA. Based on the results obtained in the in-vitro assay systems, and without wishing to be bound to any theory, it is conceivable that the effects seen in cells also resulted from dissociation of a putative IN-Rev complex by these peptides. Moreover, due probably to their ability to stimulate integration, the INS and the INr-1 and INr-2 peptides cause eventually selective death only of HIV-1 infected cells. Peptide concentrations which promote cell death are not toxic to non infected cells.

The INS and INr-1 and 2 peptides selectively kill HIV-1 infected cultured cells, while being safe to non-infected cells, and therefore can be used to specifically and selectively eliminate virus infected cells. A combination of these peptides together with an HIV-specific protease inhibitor Ro 31-8959 caused complete HIV-1 eradications (as measured by lack of integrated virus sequences and no virus production) after 12 days of administration. In addition, the INS and the INrs peptides can be used as lead peptides to obtain small molecules which will specifically and selectively eliminate of HIV-1 infected cells and thus may serve as anti-HIV-1 drug.

Furthermore, Retrovirus vectors, including those bearing the HIV integrase are being used in gene transfer and gene therapy. Since the INS and the INr-1 and INr-2 peptides stimulate the HIV-1 integrase enzymatic activity and consequently stimulate integration of the viral DNA, they may be used to enhance gene transfer and gene therapy when retroviruses vectors, especially HIV-1 derived vectors are used.

The term "inhibitor of HIV-1" according to the inventors preferably refers to any drug that decreases HIV infectivity by post integration mechanism (namely after entry, reverse transcription and integration). A non-limitative list of protease inhibitors includes: Danuravir, Saquinavir, Ritonavir, Indinavir, Nelfinavir, Amprenavir, Lopinavir, Atazanavir, Fosamprenavir, Tipranavir. A specific example is Ro 31-8959 (Saquinavir).

The method for killing HIV-1 infected cells may be in the body of an individual and in that case the "contacting" is administration to the individual of a therapeutically effective amount as described above.

It should be noted that the method of the invention is mostly active against cells containing active (infective) viruses.

The "HIV-1 infected cells" refer to any type of cells, including but not limited to: Lymphocytes, Macrophage, HeLa TZM-bl) dendritic cells etc.

The term "a peptide comprising the amino acid sequence selected from the group consisting of: WTAVQMAVFIHNFKRK (INS), WTHLEGKIILVAVHVA (INr-1) and WGSNFTSTTVKA (INr-2) or a derivative of these sequences" refers to the fact the molecule may contain within the sequence together with additional amino acid sequences or non-amino acid moieties (such as fatty acids). The additional moieties or amino acid sequences may be added to the sequence of the invention to improve one of the following: penetration (into the cell), decrease clearance, decrease degradation, improve biodistribution, biological availability and specific activity.

The term "derivative" refers to a sequence in which one or more amino acids have been deleted (from terminal or non-terminal regions), replaced (by naturally occurring, non-naturally occurring amino acids, in D or L configurations, in conservative or non-conservative substitutions), chemically modified, add (to non terminal regions), or to sequence in which the amino bonds have been chemically modified or replaced.

Typically "at least one" or "one or more" will refer to one to 6, more preferably one to five, one to four, one to three, one or two or one (deletion, addition, substitution or chemical modification).

According to the principles of the present invention the compounds and compositions of the invention are useful in indications where selective killing of virus-infected cells are beneficial.

As a result of major advances in organic chemistry and in molecular biology, many bioactive peptides can now be prepared in quantities sufficient for pharmacological and clinical use. Thus in the last few years new methods have been established for the treatment and diagnosis of illnesses in which peptides have been implicated. However, the use of peptides as therapeutic and diagnostic agents is limited by the following factors: a) tissue penetration; b) low metabolic stability towards proteolysis in the gastrointestinal tract and in serum; c) poor absorption after oral ingestion, in particular due to their relatively high molecular mass or the lack of specific transport systems or both; d) rapid excretion through the liver and kidneys; and e) undesired side effects in non-target organ systems, since peptide receptors can be widely distributed in an organism. The present invention provides bioactive peptides that overcome the disadvantages of peptides as therapeutic entities by having improved tissue penetration and target specificity.

The peptides of the present invention are preferably synthesized using conventional synthesis techniques known in the art, e.g., by chemical synthesis techniques including peptidomimetic methodologies. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984). A skilled artesian may synthesize any of the peptides of the present invention by using an automated peptide synthesizer using standard chemistry such as, for example, t-Boc or Fmoc chemistry. Synthetic peptides can be purified by preparative high performance liquid chromatography (Creighton T. 1983), and the composition of which can be confirmed via amino acid sequencing. Some of the peptides of the invention, which include only natural amino acids, may further be prepared using recombinant DNA techniques known in the art. The conjugation of the peptidic and permeability moieties may be performed using any methods known in the art, either by solid phase or solution phase chemistry. Some of the preferred compounds of the present invention may conveniently be prepared using solution phase synthesis methods. Other methods known in the art to prepare compounds like those of the present invention can be used and are comprised in the scope of the present invention. The synthetic peptides are characterized by mass spectrometry, amino acid analysis, N-terminal sequencing or by any other method known in the art.

Cyclic versions of the peptides disclosed herein are also within the scope of the present invention. Cyclization of peptides may take place by any means known in the art, for example through free amino and carboxylic groups present in the peptide sequence, or through amino acids or moieties added for cyclization. Non limiting examples of cyclization types are: side chain to side chain cyclization, C-to-N terminal cyclization, side chain to terminal cyclization, and any type of backbone cyclization incorporating at least one $N^{\alpha}$-ω-substituted amino acid residue/s as described for example in WO 95/33765.

The permeability-enhancing moiety of the conjugates of the present invention may be connected to any position in the peptide moiety, directly or through a spacer. According to a specific embodiment, the cell-permeability moiety is connected to the amino terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

DEFINITIONS

For convenience and clarity certain terms employed in the specification, examples and claims are described herein.

The term "peptide" as used herein is meant to encompass natural, non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, either the L or D isomers may be used.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, affinity to the target protein, metabolic stability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), methionine (M), Valine (V); and
6) Phenylalanine (F), Tyrosine (Y), Tryptophan (W).

Also included within the scope of the invention are salts of the peptides, analogs, and chemical derivatives of the peptides of the invention.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and /or mineralization of calcium minerals.

A "derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated. "Derivatives" of the peptides of the invention as used herein covers also derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide and do not confer toxic properties on compositions containing it. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "peptide analog" indicates molecule which has the amino acid sequence according to the invention except for one or more amino acid changes or one or more modification/replacement of an amide bond. Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

"A peptide conjugate" according to the present invention, denotes a molecule comprising an HIV-1 IN derived sequence to which another moiety, either peptidic or non peptidic, is covalently bound, directly or via a linker.

The term "linker" denotes a chemical moiety whose purpose is to link, covalently, a cell-permeability moiety and a peptide or peptidomimetic. The spacer may be used to allow distance between the permeability-enhancing moiety and the peptide, or it is a chemical bond of any type. Linker denotes a direct chemical bond or a spacer.

"Permeability" refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides, nanoparticles and liposomes.

The hydrophobic moiety according to the invention may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds.

Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethylammonium propane, trimethylammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis(dodecyaminocarbonylmethylene)-N, N'-bis((-N,N,N-trimethylammonium-ethyl-aminocarbonylmethylene)ethylenediamine tetraiodide; N,N"-Bis(hexadecylaminocarbonylmethylene)-N,N', N"-tris ((-N,N,N-trimethylammoniumethylami-nocarbonylmethylenediethylenetriamine hexaiodide; N,N"-Bis(dodecylaminocarbonylmethylene)-N,N"-bis((-N,N,N-trimethylammonium ethylaminocarbonylmethylene) cyclohexylene-1,4-diamine tetraiodide; 1,7,7-tetra-((-N,N, N,N-tetramethylammoniumethylamino-carbonylmethylene)-3-hexadecylaminocarbonyl-methylene-1,3,7-triaazaheptane heptaiodide; N,N,N',N'-tetra-((-N,N,N-trimethylammonium-ethylaminocarbonylmethylene)-N'-(1, 2-dioleoylglycero-3-phosphoethanolaminocarbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxyl-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl) carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

The term "physiologically acceptable carrier" or "diluent" or "excipient" refers to an aqueous or non-aqueous fluid that is well suited for pharmaceutical preparations. Furthermore, the term "a pharmaceutically acceptable carrier or excipient" refers to at least one carrier or excipient and includes mixtures of carriers and or excipients. The term "therapeutic" refers to any pharmaceutical, drug or prophylactic agent which may be used in the treatment (including the prevention, diagnosis, alleviation, or cure) of a malady, affliction, disease or injury in a patient.

Pharmacology

Apart from other considerations, the fact that the novel active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes novel methods are being used, in order to design and provide metabolically stable and oral bioavailable peptidomimetic analogs.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

The preferred doses for administration of such pharmaceutical compositions range from about 0.1 µg/kg to about 20 mg/kg body weight. Preferably, the amount of the active ingredient is in the range of from about 10 to 5000 µg/kg.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

EXAMPLES

The following examples demonstrate the activity of the peptides of the present invention in stimulating IN activity and selective killing of HIV-1 infected cells.

Protein Expression and Purification

Expression and purification of histidine-tagged Rev-GFP were performed as described previously (Fineberg et al., 2003, Biochemistry 42, 2625-2633). The histidine-tagged IN expression vector was a generous gift from Dr. A. Engelman (Department of Cancer Immunology and AIDS, Dana-Farber Cancer Institute, Division of AIDS, Harvard Medical School, Boston, Mass., United States of America) and its expression and purification were performed essentially as described in Jenkins et al. (1996, J Biol Chem 271, 7712-7718).

Mammalian Cultured Cells

Monolayer adherent HeLa, HEK293T, and HeLa MAGI cells (Derdeyn et al., 2000, J Virol 74, 8358-8367), expressing the β-galactosidase gene under regulation of the transactivation response element (Kimpton 1992, J Virol 66, 2232-2239) were grown in Dulbecco's Modified Eagle's Medium (DMEM). The T-lymphocyte cell lines Sup-T1 and H9 were grown in RPMI 1640 medium. Cells were provided by the NIH Reagent Program, Division of AIDS, NIAID, NIH, USA and were incubated at 37° C. in a 5% $CO_2$ atmosphere. All media were supplemented with 10% (v/v) fetal calf serum, 0.3 g/l L-glutamine, 100 U/ml penicillin and 100 U/ml streptomycin (Biological Industries, Beit Haemek, Israel).

Peptide Synthesis, Labeling and Purification

Peptides were synthesized on an Applied Biosystems (ABI) 433A peptide synthesizer. For cellular-uptake studies, the peptides were labeled with fluorescein at their N terminus (Hayouka et al., 2007, Proc Natl Acad Sci USA 104, 8316-8321). The peptides were also labeled with Trp at their N terminus for UV spectroscopy. Peptide purification was performed on a Gilson HPLC using a reverse-phase C8 semi-preparative column (ACE, advanced chromatography technologies, USA) with a gradient from 5% to 60% acetonitrile in water (both containing 0.001% v/v trifluoroacetic acid). Peptide concentrations were determined using a UV spectrophotometer (Shimadzu Kyoto, Japan) as described previously (Kohler, 1989, Plant Mol Biol 12, 189-199).

Viruses

Wild-type HIV-1 was generated by transfection (Cullen BR, 1987, Methods Enzymol 152, 684-704) of HEK293T cells with pSVC21 plasmid containing the full-length HIV-$1_{HXB2}$ viral DNA (Ratner et al., 1985, Nature 313, 277-284). Wild-type and Δenv/VSV-G (Gummuluru et al., 2000, J Virol 74, 10882-10891) viruses were harvested from HEK293T cells 48 and 72 h post-transfection with pSVC21 Δenv. The viruses were stored at −75° C.

ELISA-Based Binding Assays

Protein-peptide binding was estimated using an ELISA-based binding assay as described previously (Rosenbluh et al., 2006, Anal Biochem 352, 157-168). Briefly, Maxisorp plates (Nunc) were incubated at room temperature for 2 h with 200 μl of 10 μg/ml synthetic peptide in carbonate buffer. After incubation, the solution was removed, the plates were washed three times with PBS, and 200 μl of 10% BSA in PBS (w/v) was added for 2 h at room temperature. After rewashing with PBS, Rev-GFP, GFP alone or biotinylated-BSA-peptide conjugates (dissolved in PBS containing 10% BSA to give the appropriate concentrations), were added for further incubation for 1 h at room temperature. Following three washes with PBS, the concentration of bound biotinylated molecules was estimated after the addition of streptavidin-horseradish peroxidase (HRP) conjugate (Sigma), as described previously (Melchior et al., 1993, J Cell Biol 123, 1649-1659). The concentration of bound protein molecules was estimated after the addition of anti-GFP mouse antibody (Santa Cruz) which then was interacted with rabbit anti-mouse IgG antibody conjugated to HRP. The enzymatic activity of HRP was estimated by monitoring the product's optical density (OD) at 490 nm using an ELISA plate reader (Tecan Sunrise). Each measurement was performed at least in duplicate.

Determination of Integrase Activity

The IN enzymatic activity assay was performed using a previously described assay system (Craigie et al., 1991, Nucleic Acids Res 19, 2729-2734, Hwang et al., 2000, Nucleic Acids Res 28, 4884-4892). Briefly, the oligonucleotide substrate consisted of one oligo (5'-ACTGCTAGAGATTTTCCACACTGACTAAAAGGGTC-3') labeled with biotin at the 3' end and the other oligo (5'-GACCCTTTTAGTCAGTGTGGAAAATCTCTAGCAGT-3') labeled with digoxigenin at the 5' end. When inhibition was studied, the IN was preincubated with the peptide or protein for 15 min prior to addition of the DNA substrate. The entire IN reaction was followed by immunosorbent assay on avidin-coated plates as described previously (Rosenbluh et al., 2007, J Biol Chem 282, 15743-15753).

Cell-Penetration Experiments

Fluorescein-labeled peptides at a final concentration of 10 μM in PBS were incubated with HeLa cells for 1 h at 37° C. After three washes in PBS, cells were visualized by a confocal microscopy as described previously (Rosenbluh et al., 2007, J Biol Chem 282, 15743-15753).

Effect of Peptides on Cell Viability Using the MTT (3-(4,5-dimethylthiazol-2-yl)-2,5-diphenyltetrazolium bromide) Assay Following incubation of the cells with the indicated peptides, the medium was removed and the cells were further incubated in Earl's solution containing 0.3 mg/ml MTT for 1 h. Subsequently, the solution was removed and the cells were dissolved in 100 μl DMSO for 10 min at room temperature. The DMSO-solubilized cells were transferred to a 96-well ELISA plate and OD values were monitored at a wavelength of 570 nm.

HIV-1 Titration by Multinuclear Activation of a Galactosidase Indicator (MAGI) Assay Quantitative titration of HIV-1 was carried out using the MAGI assay, as described by Kimpton and Emerman (J Virol 1992, 66, 2232-2239). Briefly, TZM-bl cells were grown in 96-well plates at $1 \times 10^4$ cells per well and following 12 h incubation at 37° C., peptides were added; after an additional 2 h of incubation, the cells were infected with 50 μl of serially diluted virus (HIV-1 Δenv/VSV-G or wild-type HIV-1 which was obtained from infected lymphocytes every 2 days) as described (Kimpton 1992, J Virol 66, 2232-2239). Two days post-infection (PI), cultured cells were fixed and β-galactosidase was estimated as described above. Blue cells were counted under a light microscope at 200× magnification.

Infection of Cultured Lymphocyte Cells with HIV-1

Cultured lymphocytes ($1 \times 10^5$) were centrifuged for 5 min at 2000 rpm and after removal of the supernatant, the cells were resuspended in 0.2 to 0.5 ml of RPMI 1640 medium containing virus at a multiplicity of infection (MOI) of 0.01, 0.1 and 5. Following absorption for 2 h at 37° C., the cells were washed to remove unbound virus and then incubated at the same temperature for an additional 1 to 8 days.

Quantitative Estimation of HIV-1 Infection by Determination of Extracellular p24

Lymphoid cells were incubated with the indicated peptides for 2 h and following infection with wild-type HIV-1 at a MOI of 0.01 (as described above), the cells were incubated for 8 days, or 48 h at a MOI of 1. The amount of p24 protein was estimated in the cell medium every 2 days exactly as described previously.

PCR Analysis of Early Viral Genes

Sup-T1 cells were incubated with 12.5 μM of peptides or with 2 μM azidothymidine (AZT) for 2 h and then were infected with HIV-1 Δenv/VSV-G virus at a MOI of 2, and further incubated for 6 h. The viral Gag or Nef DNA sequences were amplified using specific primers: Gag-specific primers, 5'-AGTGGGGGGACATCAAGCAGCCATG-3' and 5'-TGCTATGTCAGTTCCCCTTGGTTCTC-3', and Nef-specific primers, 5'-CCTGGCTAGAAGCACAAGAG-3' and 5'-CTTGTAGCAAGCTCGATGTC-3'. The fragments were amplified from 10 ng of total cell DNA in a 25-μl reaction mixture containing 1× PCR buffer, 3.5 mM $MgCl_2$, 200 μM dNTPs, 300 nM primers, and 0.025 units/μl of Taq polymerase. The PCR conditions were as follows: a DNA denaturation and polymerase activation step of 5 min at 95° C. and then 29 cycles of amplification (95° C. for 45 s, 60° C. for 30 s, 72° C. for 45 s).

Quantitative Analysis of the Copy Numbers of HIV-1 DNA Integrated into Cellular Genome The integration reaction was estimated essentially as described previously (Rosenbluh et al., 2007, J Biol Chem 282, 15743-15753). Briefly, following incubation of the indicated peptides with H9 or Sup-T1 cells for 2 h, the cells were infected with a HIV-1 Δenv/VSV-G virus at a MOI of 5 (as described above) for 24 h or with wild-type HIV-1 at a MOI of 0.01 for 8 days. Integrated HIV-1 sequences were amplified by two PCR replication steps using the HIV-1 LTR-specific primer (LTR-TAG-F 5'-ATGCCACGTAAGCGAAACTCTGGCTAACTAGGGAACCCACTG-3') and Alu-targeting primers (first-Alu-F 5'-AGCCTCCCGAGTAGCTGGGA-3' and first-Alu-R 5'-TTACAGGCATGAGCCACCG-3') (Yamamoto et al., 2006, Virus Genes 32, 105-113). Alu-LTR fragments were amplified from 10 ng of total cell DNA in a 25-μl reaction mixture containing 1× PCR buffer, 3.5 mM $MgCl_2$, 200 μM dNTPs, 300 nM primers, and 0.025 units/μl of Taq polymerase. The first-round PCR cycle conditions were as follows: a DNA denaturation and polymerase activation step of 10 mM at 95° C. and then 12 cycles of amplification (95° C. for 15 s, 60° C. for 30 s, 72° C. for 5 min).

During the second-round PCR, the first-round PCR product could be specifically amplified by using the tag-specific primer (tag-F 5'-ATGCCACGTAAGCGAAACTC-3') and the LTR primer (LTR-R 5'-AGGCAAGCTTTATTGAGGCT-TAAG-3') designed by PrimerExpress (Applied Biosystems) using default settings. The second-round PCR was performed on ½₅ th of the first-round PCR product in a mixture containing 300 nM of each primer, 12.5 µl of 2× SYBR Green master mixture (Applied Biosystems) at a final volume of 25 µl, run on an ABI PRIZM 7700 (Applied Biosystems). The second-round PCR cycles began with DNA denaturation and a polymerase-activation step (95° C. for 10 min), followed by 40 cycles of amplification (95° C. for 15 s, 60° C. for 60 s).

For generation a standard calibration curve, the SVC21 plasmid containing the full-length HIV-1$_{HXB2}$ viral DNA was used as a template. In the first-round PCR, the LTR-TAG-F and LTR-R primers were used and the second-round PCR was performed using the tag-F and LTR-R primers. The standard linear curve was in the range of 5 ng to 0.25 fg (R=0.99). DNA samples were assayed with quadruplets of each sample. The cell equivalents in the sample DNA were calculated based on amplification of the 18S gene by real-time PCR as described in (Field et al, 2002, Biochem J 368, 855-864).

All the results described in the examples are averages of at least three determinations, where the standard deviation never exceeded ±20%.

Example 1

Selection of IN-Derived Peptides

Figure 1B:
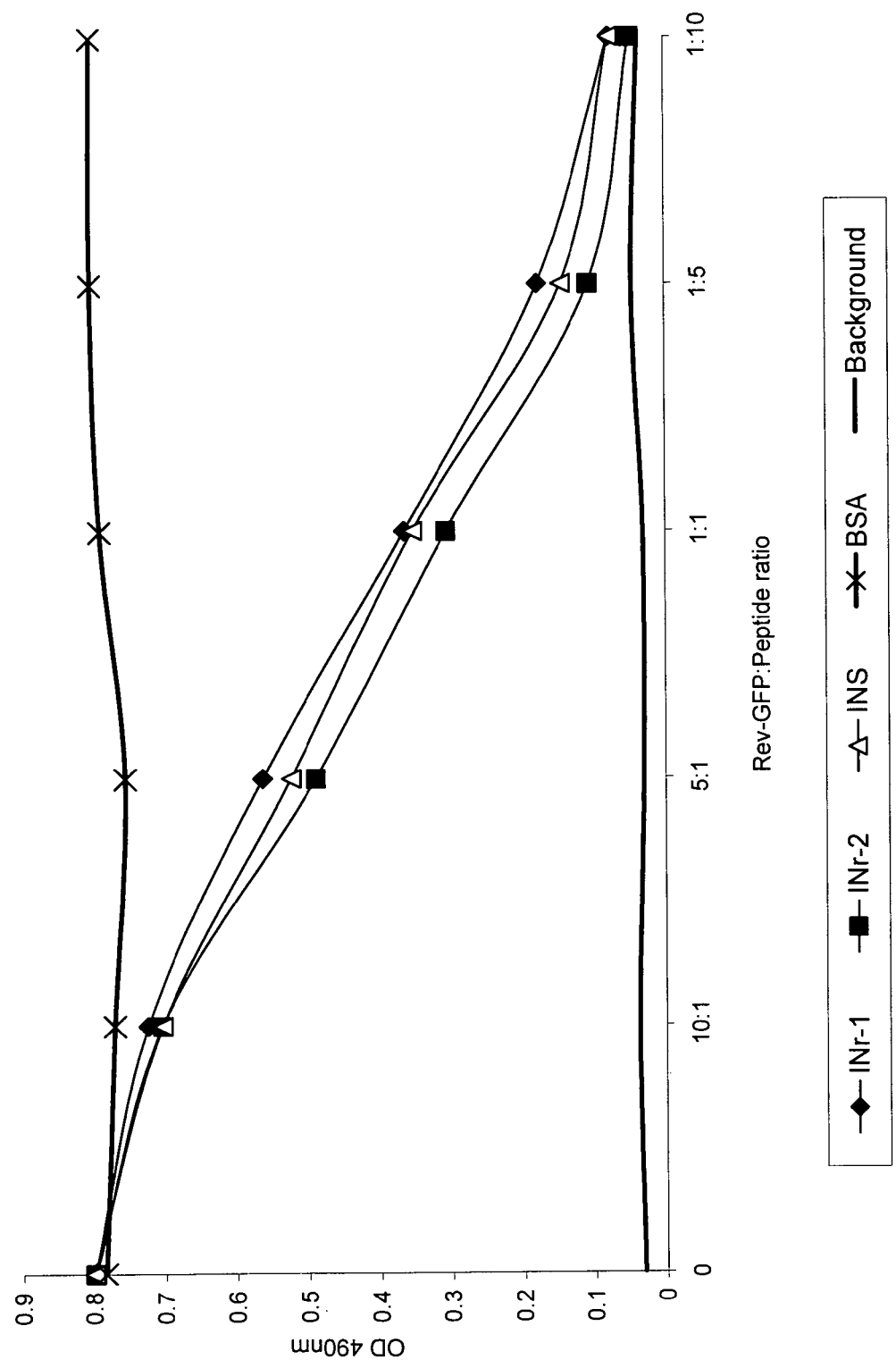
Figure 1C:
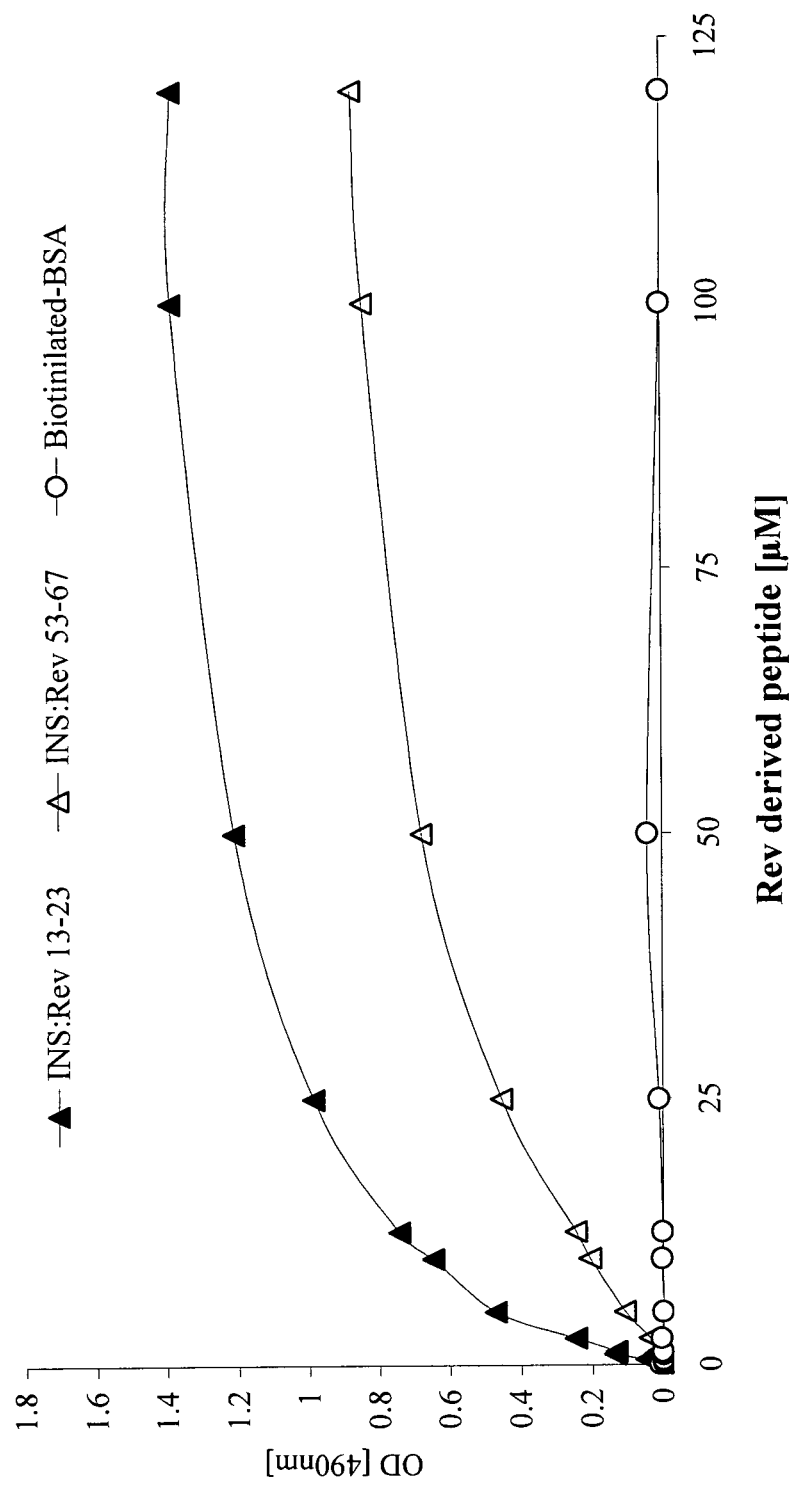
Figure 1D:
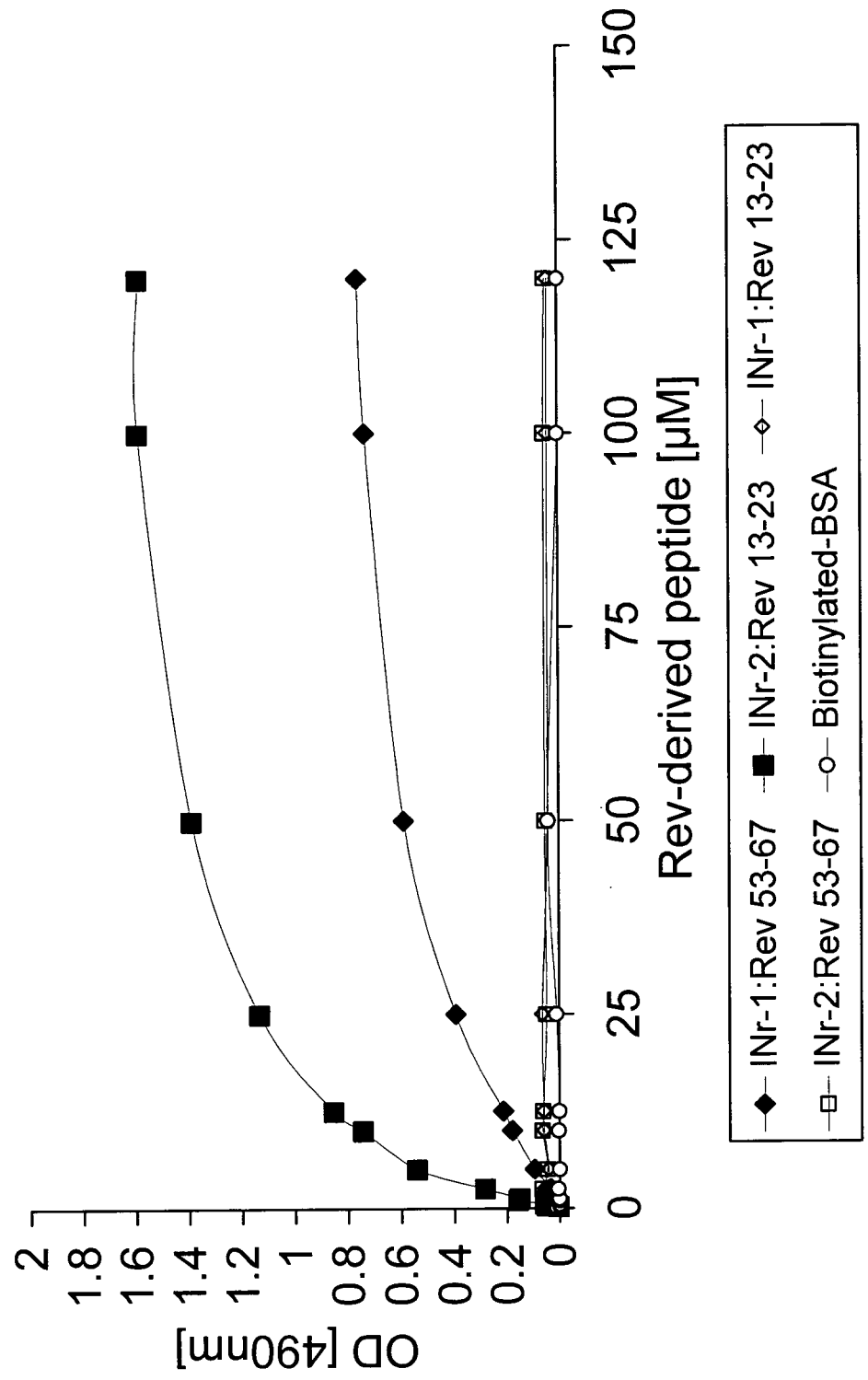

Selection of peptide sequences that interact with the Rev protein, Rev-derived peptides, and the IN itself was made by screening of an IN peptide library (NIH AIDS Research and Reference Reagent Program, Division of AIDS, NIAID, NIH: HIV-1 Consensus B Pol (15-mer) peptides—Complete Set from DAIDS, NIAID), using an ELISA-based assay system. Three IN-derived peptides (INS, INr-1, INr-2), were identified as specifically interacting with Rev protein labeled with green florescent protein (Rev-GFP). One of the identified peptides (INS) was found to interact also with the IN protein itself. The amino acid sequence and the binding patterns of the identified peptides are shown in Table 1 and FIG. 1A. The results in FIG. 1B show that addition of INS or INrs peptides to the complex formed between IN and Rev-GFP induces the release of the bound Rev-GFP. This observation further confirmed that the sequence of the INS and INrs peptides within the IN protein mediate the interaction with the Rev protein. The INS peptide interacted with both Rev 13-23 and Rev 53-67 peptides while INr-1 and INr-2 interacted with the Rev 53-67 and Rev 13-23 peptides respectively (FIG. 1D and Table 1). As shown in FIG. 1D, INr-1 interacted with the Rev 53-67 peptide but not with the Rev 13-23 peptide, while INr-2 interacted with Rev 13-23 but not with Rev 53-67, indicating specificity of interaction. This was inferred from experiments showing that biotinylated-BSA-Rev 13-23 or Rev 53-67 conjugates were able to interact with INS or INrs peptides-coated plates (FIGS. 1C and 1D). No binding was observed with the control biotinylated-BSA alone (FIGS. 1C and 1D), indicating specific binding to the INS peptide.

FIG. 1: 1A—Rev-GFP or GFP alone were incubated in ELISA plates coated with either INr-1 (♦, ◇, respectively), INr-2 (■, □, respectively) or INS (▲, Δ, respectively) and binding was determined as described above. 1B—The IN protein was first bound to the ELISA plate and then incubated with Rev-GFP to obtain a Rev-IN complex. The complex was then incubated with either one of the INr peptides or the INS peptide at the designated Rev-GFP:peptide ratio. Wells were then washed and the amount of bound Rev-GFP was determined by mouse anti-GFP antibody and secondary rabbit anti-mouse HRP-conjugated antibody. 1C—Rev 13-23 and Rev 53-67 (conjugated to biotinylated-BSA) (▲, Δ respectively) were incubated in ELISA plates coated with INS and binding was estimated as described in Materials and Methods. 1D—Rev 13-23 and Rev 53-67 (conjugated to biotinylated-BSA) were incubated in ELISA plates coated with either INr-1 (◇, ♦, respectively) or INr-2 (■, □, respectively) and binding was estimated as described above. All other experimental conditions were as described previously (Armon-Omer et al., 2008, J Mol Biol 376, 971-982) and above.

TABLE 1

| Name | Sequence | SEQ ID NO. | IN residues | Bind |
|------|----------|------------|-------------|------|
| INS | WTAVQMAVFIHNFKRK | 6 | W(174-188) | IN<br>Rev-GFP<br>Rev 13-23<br>Rev 53-67 |
| INr-1 | WTHLEGKIILVAVHVA | 7 | W(66-80) | Rev-GFP<br>Rev 53-67 |
| INr-2 | WGSNFTSTTVKA | 5 | W(118-128) | Rev-GFP<br>Rev 13-23 |

Example 2

Figure 2A:
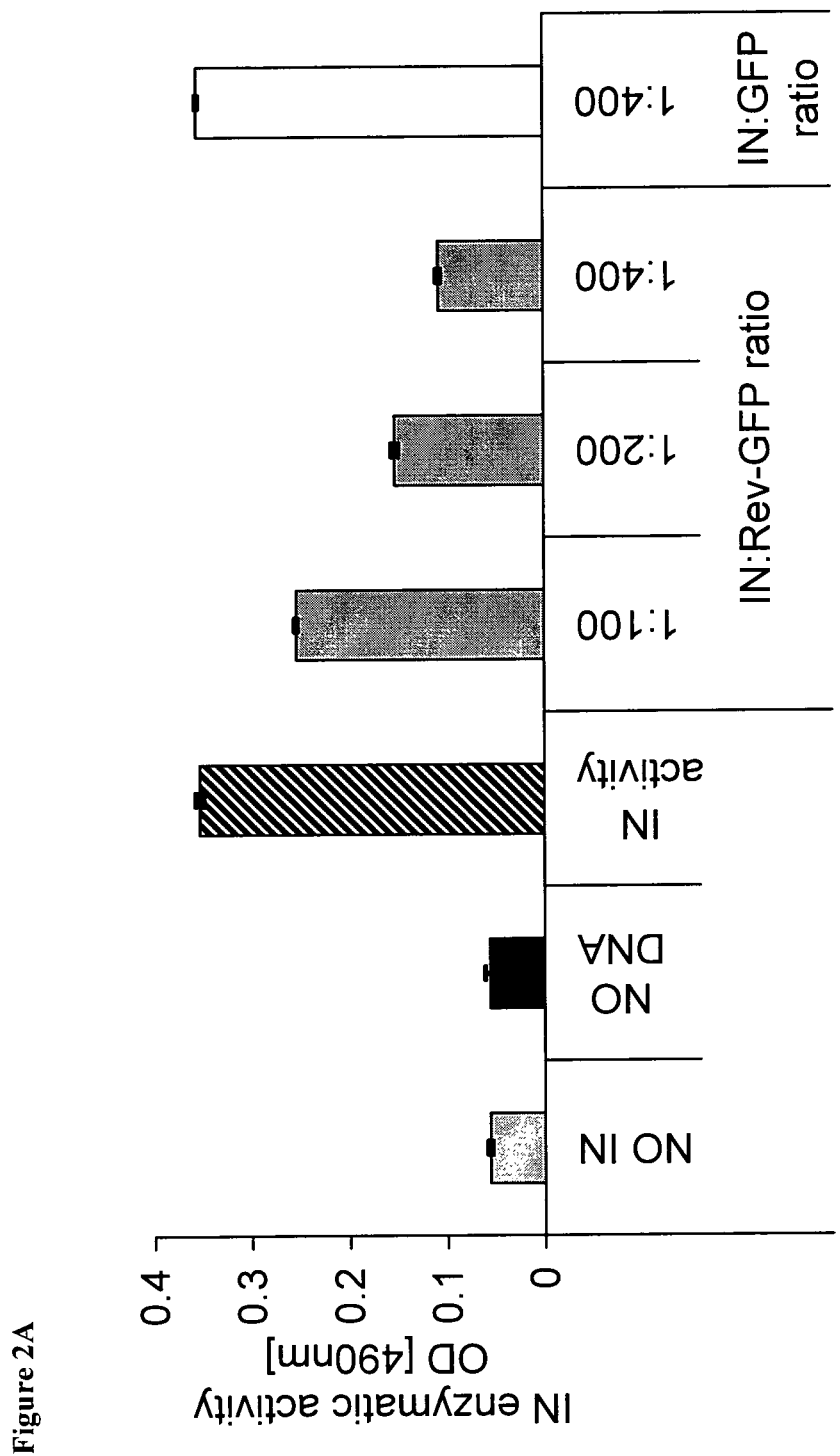
FIGS. 2A-2C represent inhibition of IN enzymatic activity by Rev and its abrogation by the INS and the INrs peptides: (A) Rev-GFP or GFP incubated with different molar ratios of IN (390 nM) and the IN enzymatic activity was determined (B) Rev-GFP preincubated with the INS peptide at a molar ratio of 5:1 (peptide:Rev-GFP) and the resultant mixture was added to a solution containing IN to give a molar ratio of 1:200 and 1:400 (IN:Rev-GFP). Following an incubation period, IN activity determined. (C) Same as (B) but with the INrs peptides.
Figure 2B:
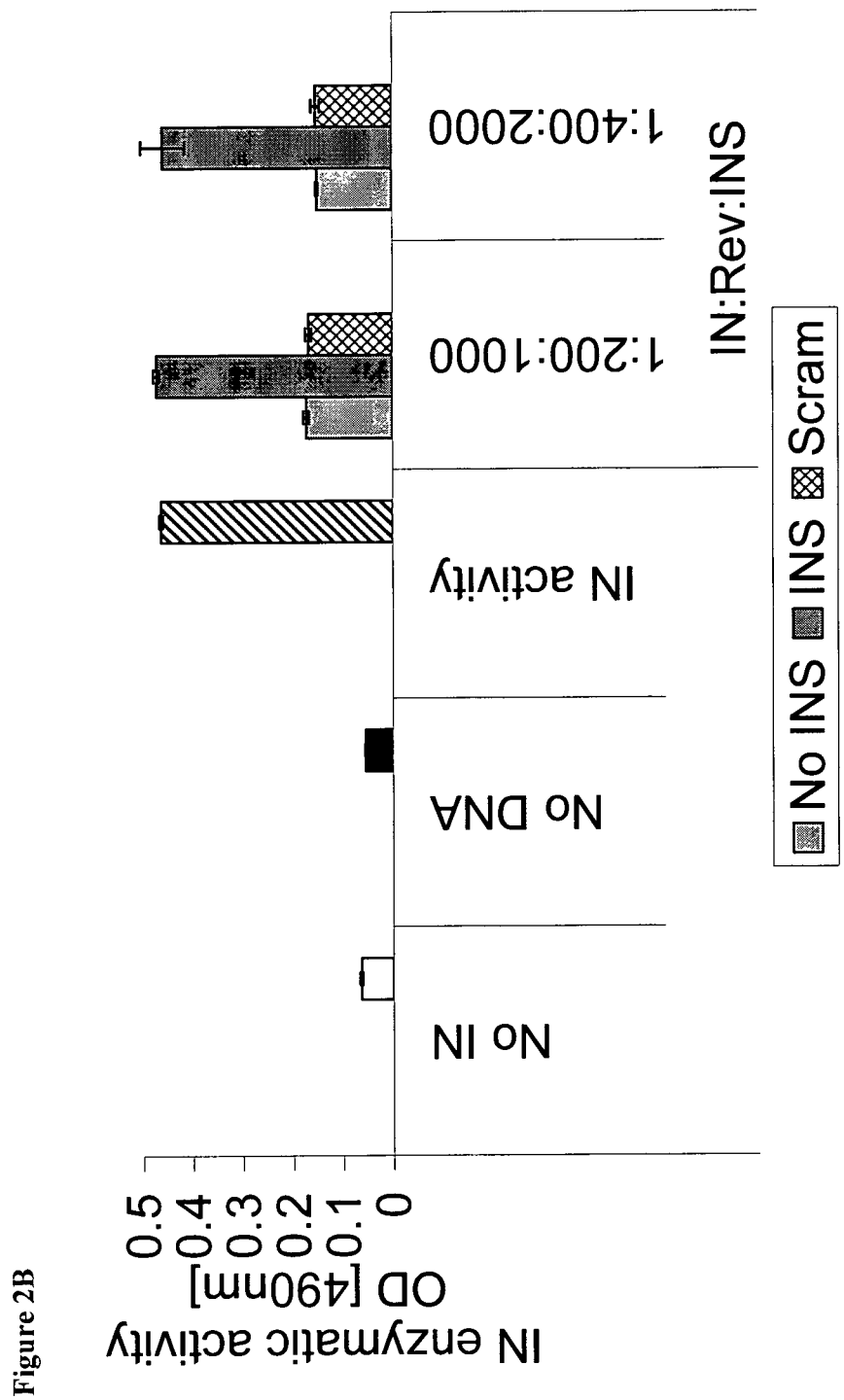
Figure 3A:
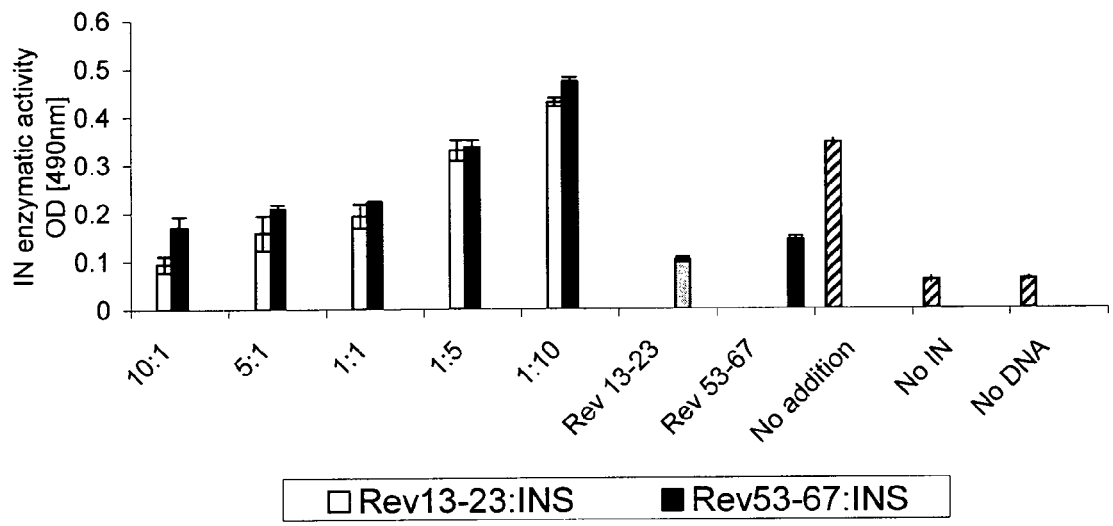
FIGS. 3A-3C demonstrate inhibition of IN activity by Rev- and Rev-derived peptides, and specific abrogation by the INS and the INr peptides. IN (390 nM) incubated with 50 μM of the Rev-derived peptides (Rev 13-23 or Rev 53-67, 1:300 IN:Rev-derived peptide) peptides added at several molar ratios (10:1 to 1:10 Rev peptide:IN peptide): (A) Rev-peptides with INS; (B) Rev13-23 with INr-1 and INr-2; and (C) Rev53-67 with INr-1 and INr-2.
Figure 3B:
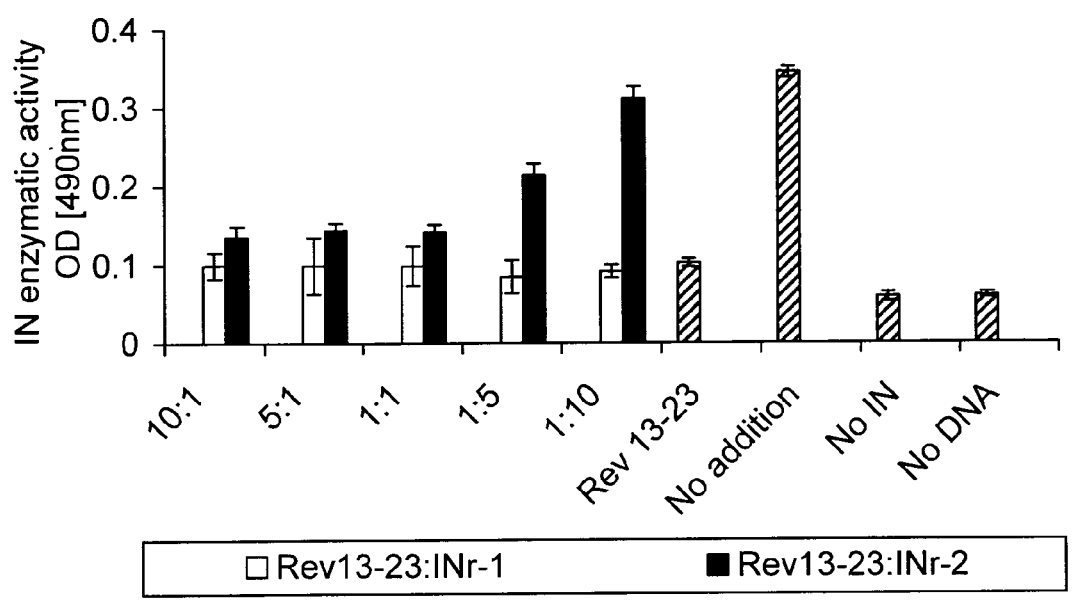
Figure 3C:
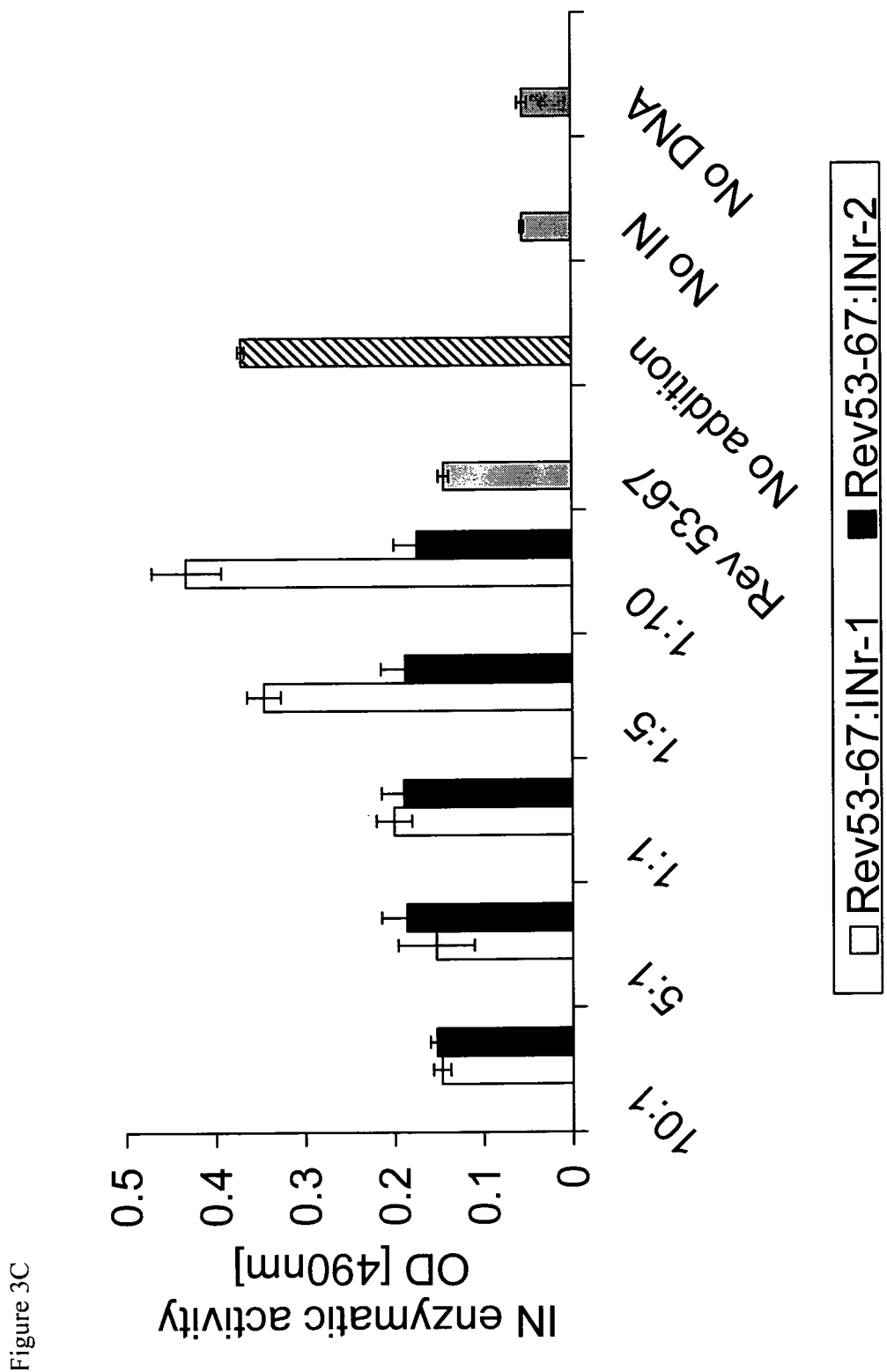

Specific Abrogation of the Inhibitory Effect of the Rev Protein and Rev-Derived Peptides on IN Enzymatic Activity, by the INS and INrs Peptides The results depicted in FIG. 2A clearly show that the enzymatic activity of IN is inhibited by Rev-GFP (GFP designates Green fluorescent protein used to label the protein/peptide) due to specific interaction with the Rev protein itself and not with the GFP (FIG. 2A). At a Rev-GFP:IN (mole/mole) ratio of about 100, approximately 30% inhibition was already observed, reaching up to 70% inhibition at a ratio of 400 (FIG. 2A). Interestingly, the INS and INrs peptides abrogated the inhibitory activities of Rev-GFP (FIGS. 2B and C). The results in FIG. 3 confirm previously described results (Rosenbluh et al., 2007, J Biol Chem 282, 15743-15753) showing that the Rev-derived peptides (Rev 13-23 and Rev 53-67 blocked IN enzymatic activity, reaching 60 to 70% inhibition at a peptide:IN (mol/mol) ratio of about 150 (FIG. 3). It is also evident that the INS and INrs peptides were able to abrogate the inhibitory effect of the Rev derived peptides on integrase activity. Integrase activity was fully restored in the presence of the INS peptide at a molar ratio of Rev:INS peptide of 1:5 and even stimulate the IN activity at a molar ratio of 1:10 (FIG. 3A). As expected from their interaction specificity (see Table 1) INr-1 abrogated the inhibitory effect of the Rev 53-67 peptide while INr-2 that exerted by the Rev 13-23 peptide and fully restored the integrase activity at a molar ratio of 1:10 (FIGS. 3B and C). This appeared to be due to the ability of the INS to specifically interact with Rev-GFP and the Rev-derived peptides, since incubation with a scrambled peptide did not restore the integrase activity (FIGS. 2B and C).

Figure 2C:
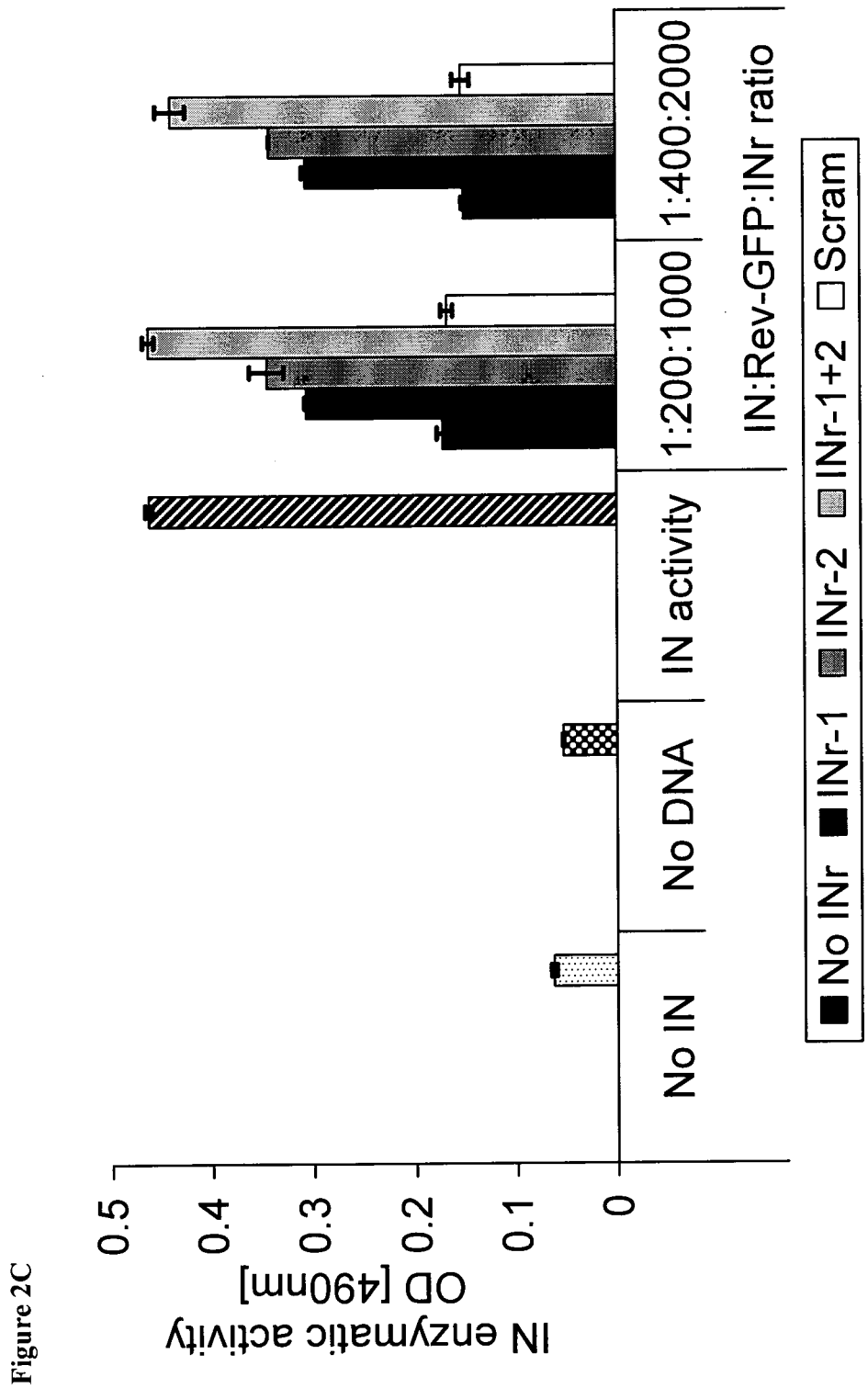

FIG. 2 (A) Rev-GFP (dark green) or GFP (turquoise) were incubated at different molar ratios with IN (390 nM) and the IN enzymatic activity was determined as described above. (B) Rev-GFP was preincubated with the indicated INS peptide at a molar ratio of 5:1 (peptide:Rev-GFP) and the resultant mixture was added to a solution containing IN to give a molar ratio of 1:200 and 1:400 (IN:Rev-GFP). Following an incubation period, IN activity was estimated as described above. (C) Same as (B) but with the INrs peptides.

FIG. 3 A-C IN (390 nM) was incubated with 50 µM of the Rev-derived peptides (1:300 IN:Rev-derived peptide, Rev13-23 or Rev 53-67) and then the INS peptide was added at different molar ratios ranging from 10:1 to 1:10 (Rev peptide:INS peptide) (A) IN (390 nM) was incubated with 50 µM of the Rev-derived peptides (1:300 IN:Rev-derived peptide), (Rev13-23 (B) and Rev 53-67 (C)) and then the INr peptides were added at different molar ratios ranging from 10:1 to 1:10 (Rev peptide:INr peptide).

Example 3

Figure 4A:
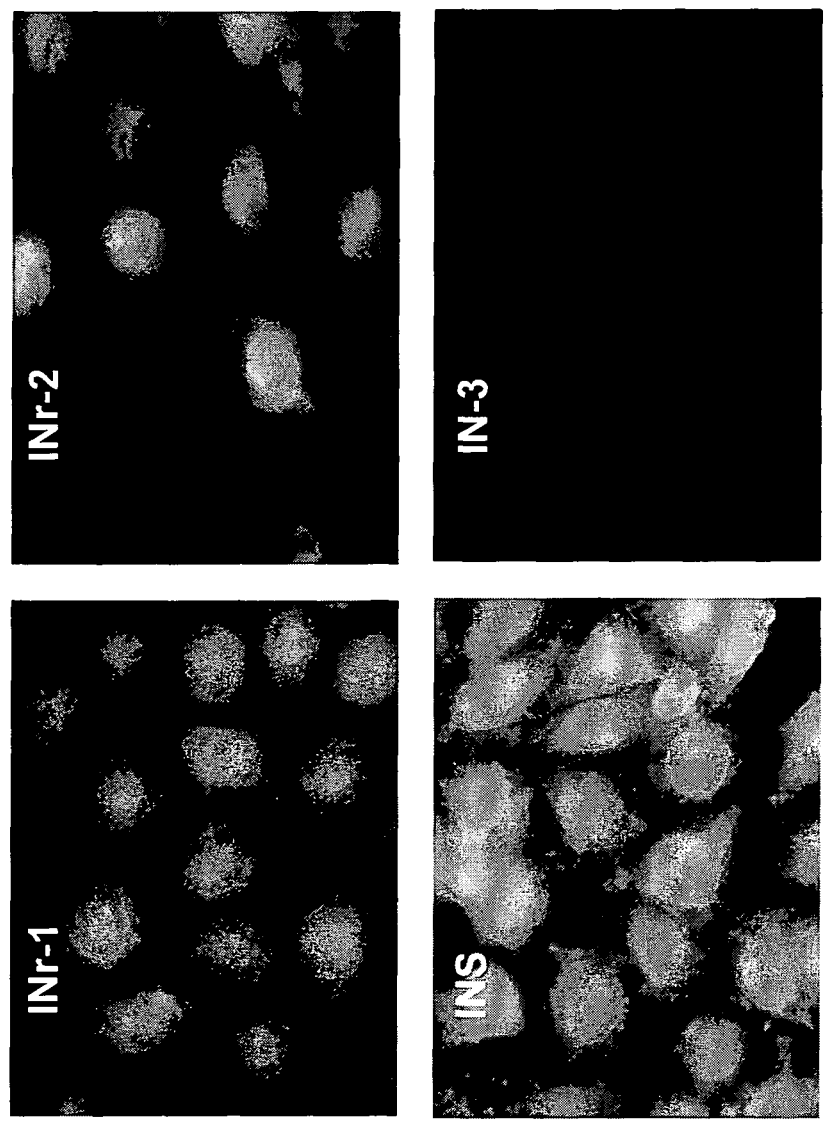
FIGS. 4A-4C show cell penetration and lack of toxicity of the peptides: (A) Fluorescein-labeled peptides (10 μM) of INr-1, INr-2, INS or IN-3 (control non permeable peptide) penetration into HeLa cells as visualized by a confocal microscope. (B) lack of cell toxicity of the peptides to HeLa TZM-bl cells; (C) lack of cell toxicity of the peptides to H9 lymphocytes.
Figure 4B:
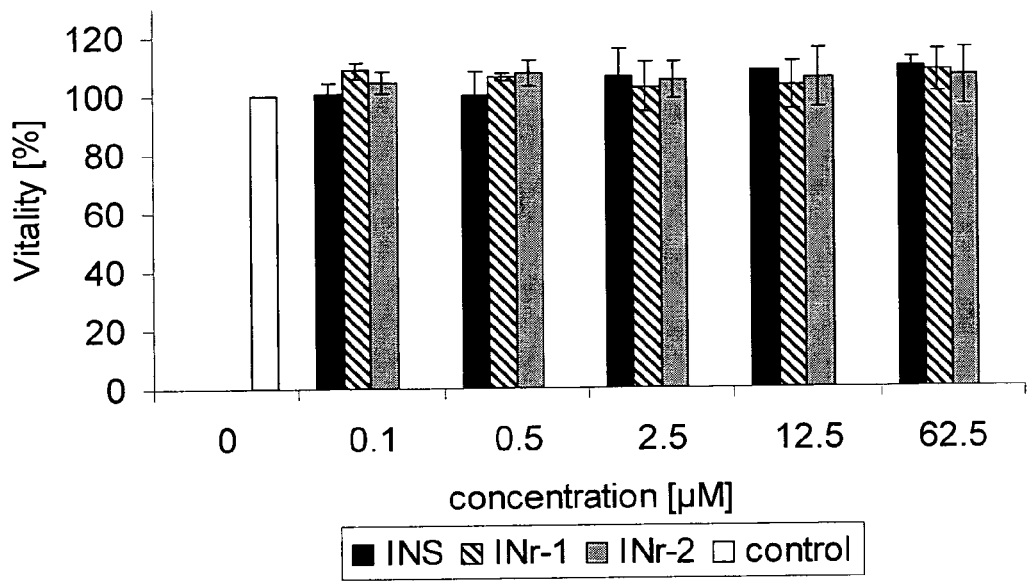
Figure 4C:
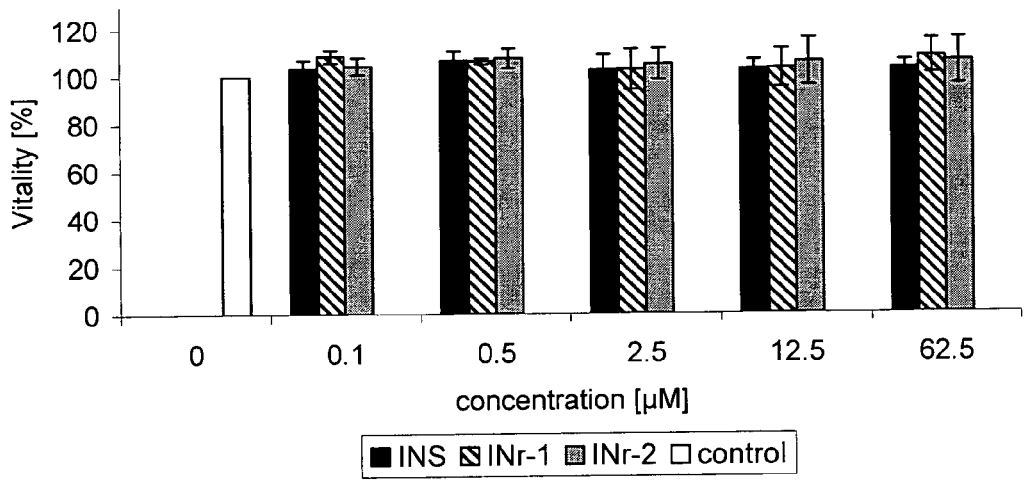

The INS and INrs Peptides are Cell Permeable and Stimulates Virus Production and Integration of the HIV-1 Genome in Cultured Cells It is evident from the results shown in FIG. 4A that the INS and INrs peptides are cell-permeable peptides. The results further demonstrates that another peptide having the sequence RCWLQMWQESFDLVAMLGDT (SEQ ID NO:8), designated IN-3 (Armon-Omer et al., 2008, J Mol Biol 376, 971-982), of about the same size, failed to penetrate the cultured HeLa cells clearly indicate the integrity of the cells' plasma membranes as well as their viability (see also FIGS. 4B and C). No toxic effect was observed when these three peptides were incubated, up to about 62 µM, with either HeLa TZM-bl cells (FIG. 4B) or H9-T-cell lymphocytes (FIG. 4C).

Figure 5A:
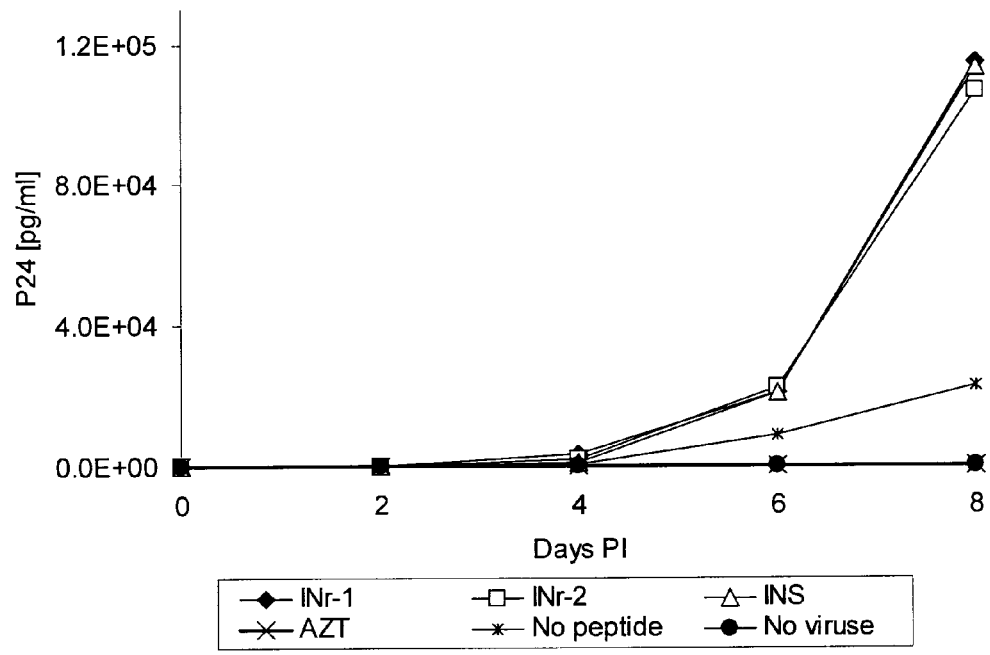
FIG. 5A-5D depict the effect of INS and INrs peptides on HIV-1 infection in comparison with the inhibitor azidothymidine (AZT). The peptides (12.5 μM), or AZT (2 μM), were incubated with H9 cells (A and C) and Sup-T1 lymphocyte cells (B and D) which were then infected with HIV-1. The amount of viral P24 (A and B) and virus titer (C and D) were determined.
Figure 5B:
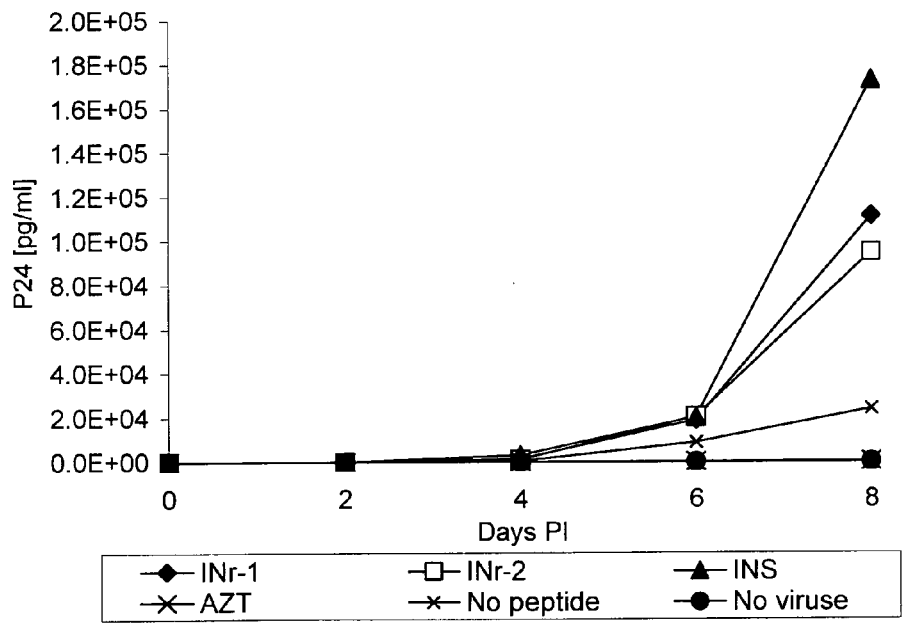
Figure 5C:
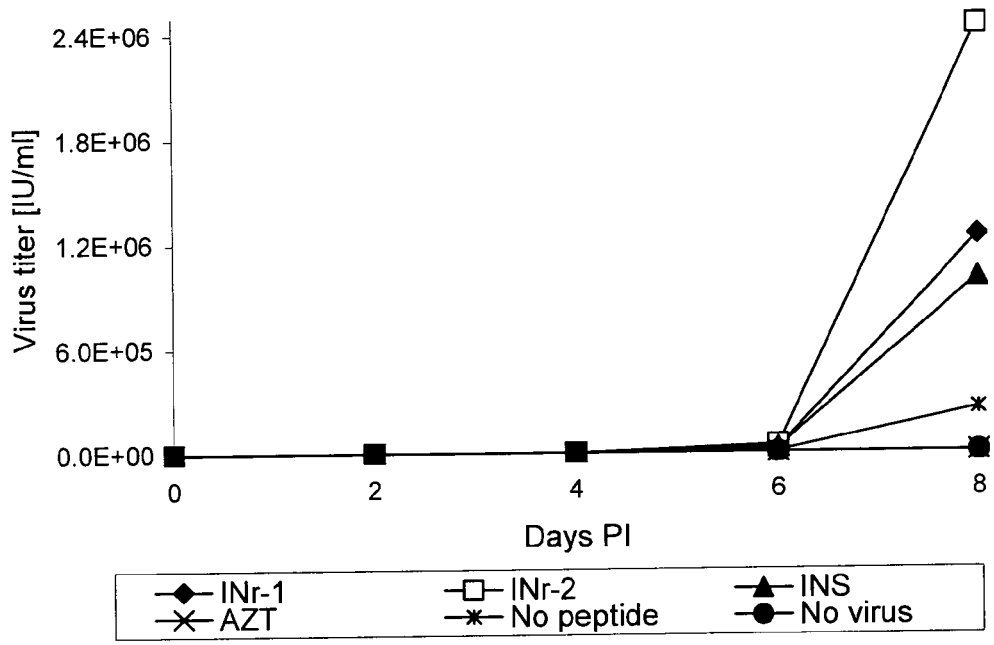
Figure 5D:
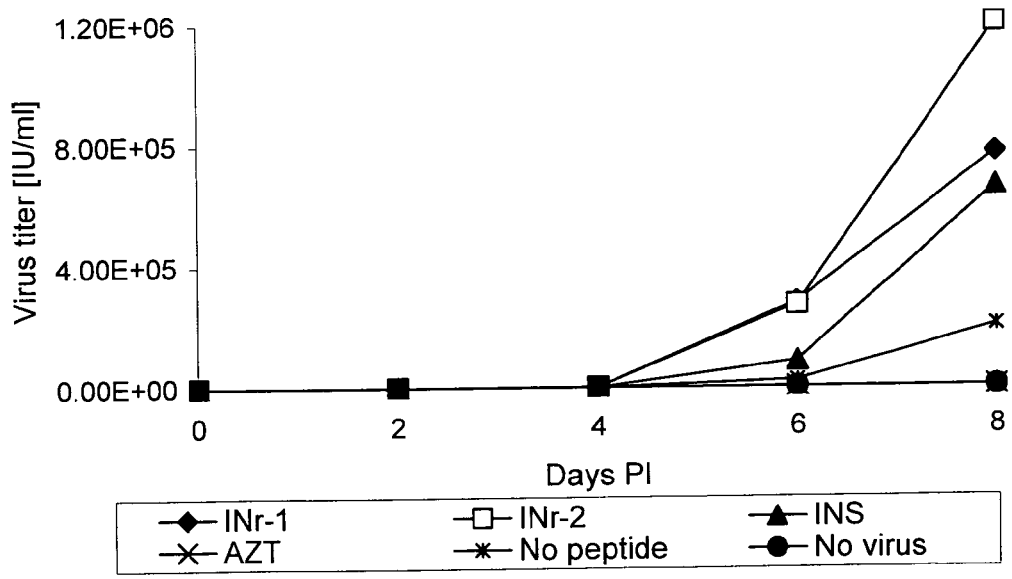

Stimulation of virus integration by the INS and INrs peptides was observed when it was assayed by the appearance of the viral p24 antigen in H9 and Sup-T1 cultured cells (FIGS. 5A and B). The same stimulation was also observed when the efficiency of infection was determined by the appearance of infectious viral particles (FIGS. 5C and D).

Figure 6A:
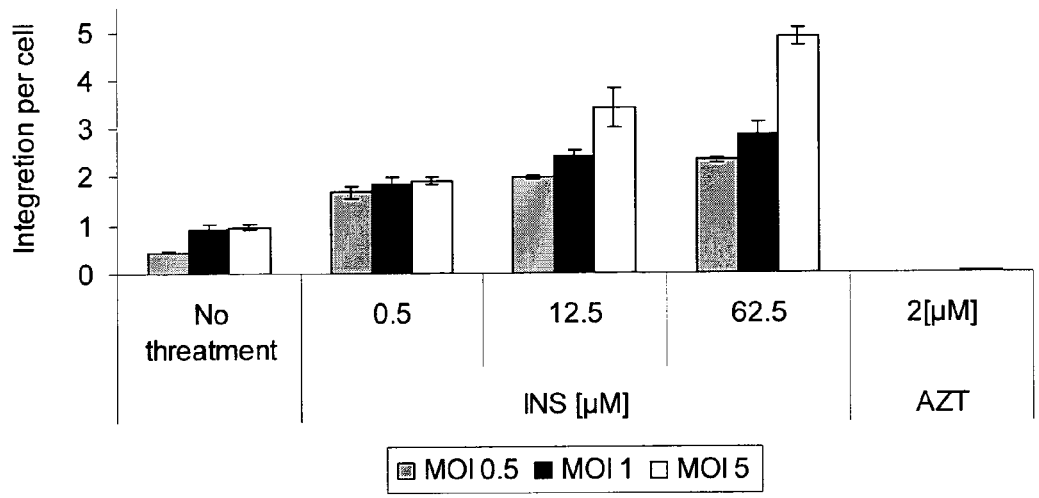
FIG. 6A-6B stimulation of viral DNA integration events by the INS and INrs peptides in H9 T-lymphoid cells (A) different concentrations of the INS peptide and AZT (2 μM); (B) INr-1, INr-2 and combination of these peptides (12.5 μM) or AZT (2 μM).
Figure 6B:
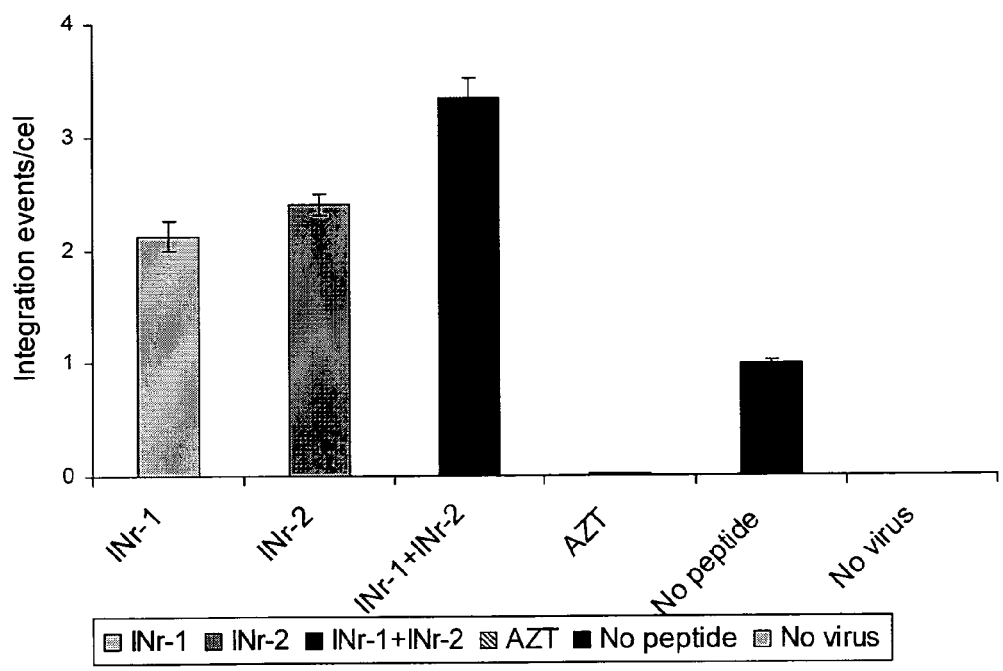

Stimulation of the integration process by the INS and INrs peptides was observed when insertion of the viral DNA into the host DNA was estimated directly 24 hours post infection (PI). As can be seen in FIG. 6, a ca. 2- to 5-fold stimulation of integration per cell was obtained following a single cycle of viral infection with INS (FIG. 6A) and with INrs (FIG. 6B).

FIG. 4 (A) Fluorescein-labeled peptides (10 µM) of INr-1, INr-2, INS or IN-3, non permeable peptide were incubated for 2 h at 37° C. with HeLa cells. The cells were then washed three times with PBS and visualized by a confocal microscope. (B) Cell toxicity as was determined by the MTT assay, the INS and INrs peptides were found to be non-toxic in the measured concentrations in HeLa TZM-bl cells. (C) same as (B) but in H9 lymphocytes FIG. 5 A-D The INrs or INS (12.5 µM) were incubated with H9 cells (A and C) and Sup-T1 lymphocyte cells (B and D) which were then infected with HIV-1 as described above. The amount of viral P24 (A and B) and virus titer (C and D) were determined every 2 days by ELISA and MAGI assay (Kimpton 1992, J Virol 66, 2232-2239), respectively. The concentration of azidothymidine (AZT) used was 2 µM.

FIG. 6 (A) H9 T-lymphoid cells were incubated with the INS peptide in the designated concentrations or AZT (2 µM) and following HIV-1 infection, the integrated viral DNA/cell was assessed by real-time PCR following a single cycle of infection at a MOI 0.5 to 5 of Δenv/VSV-G HIV-1. (B) H9 T-lymphoid cells were incubated with the indicated peptides (12.5 µM) or AZT (2 µM) and following HIV-1 infection, the integrated viral DNA/cell was assessed by real-time PCR following a single cycle of infection at a MOT of 5 of Δenv/VSV-G HIV-1.

Example 4

Figure 7:
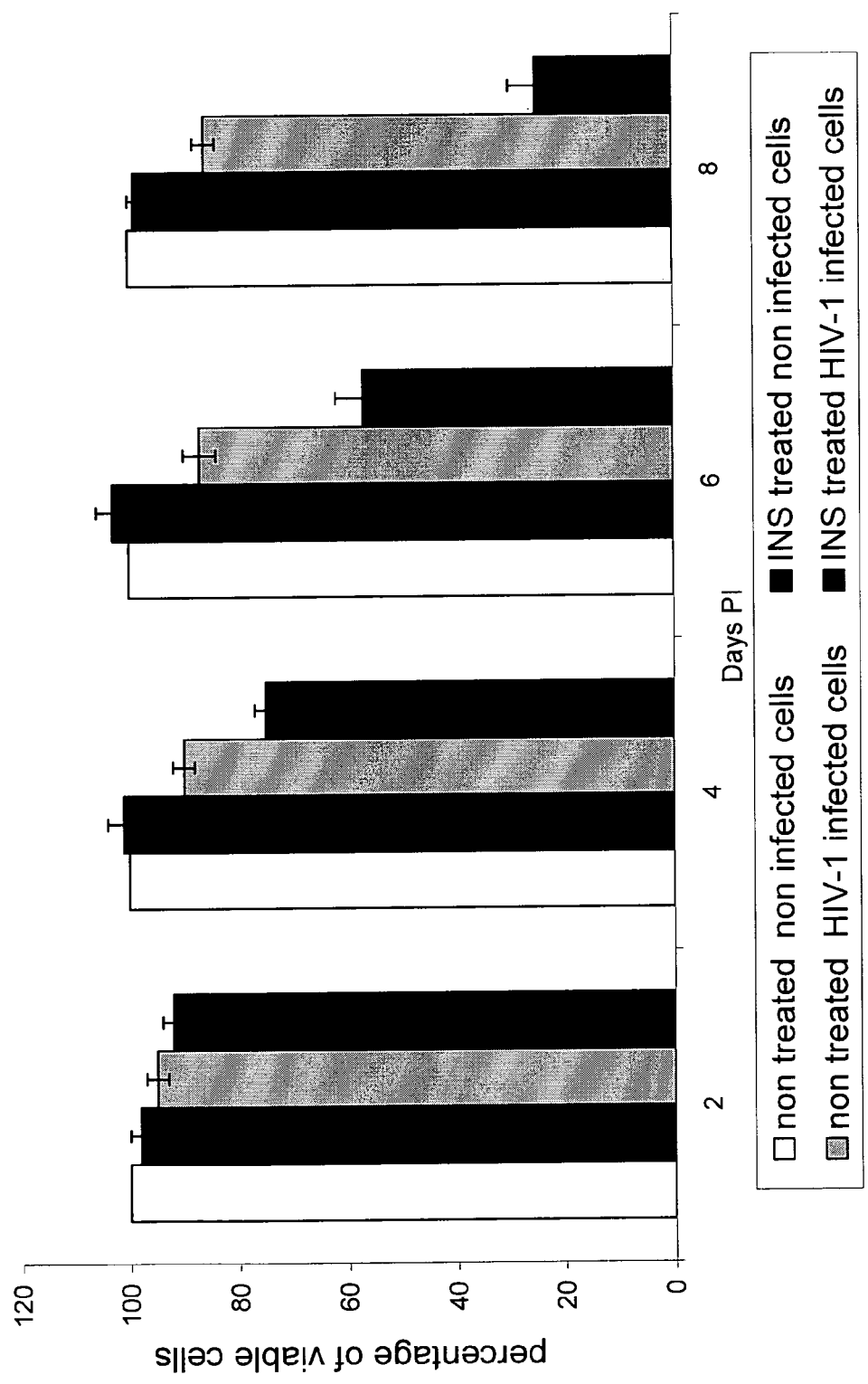
FIG. 7 represents survival of HIV-1 infected Hela cells following treatment with the peptide INS. Cells were infected with WT HIV-1 at MOI of 0.01 and 12.5 μM of INS were added.
Figure 8:
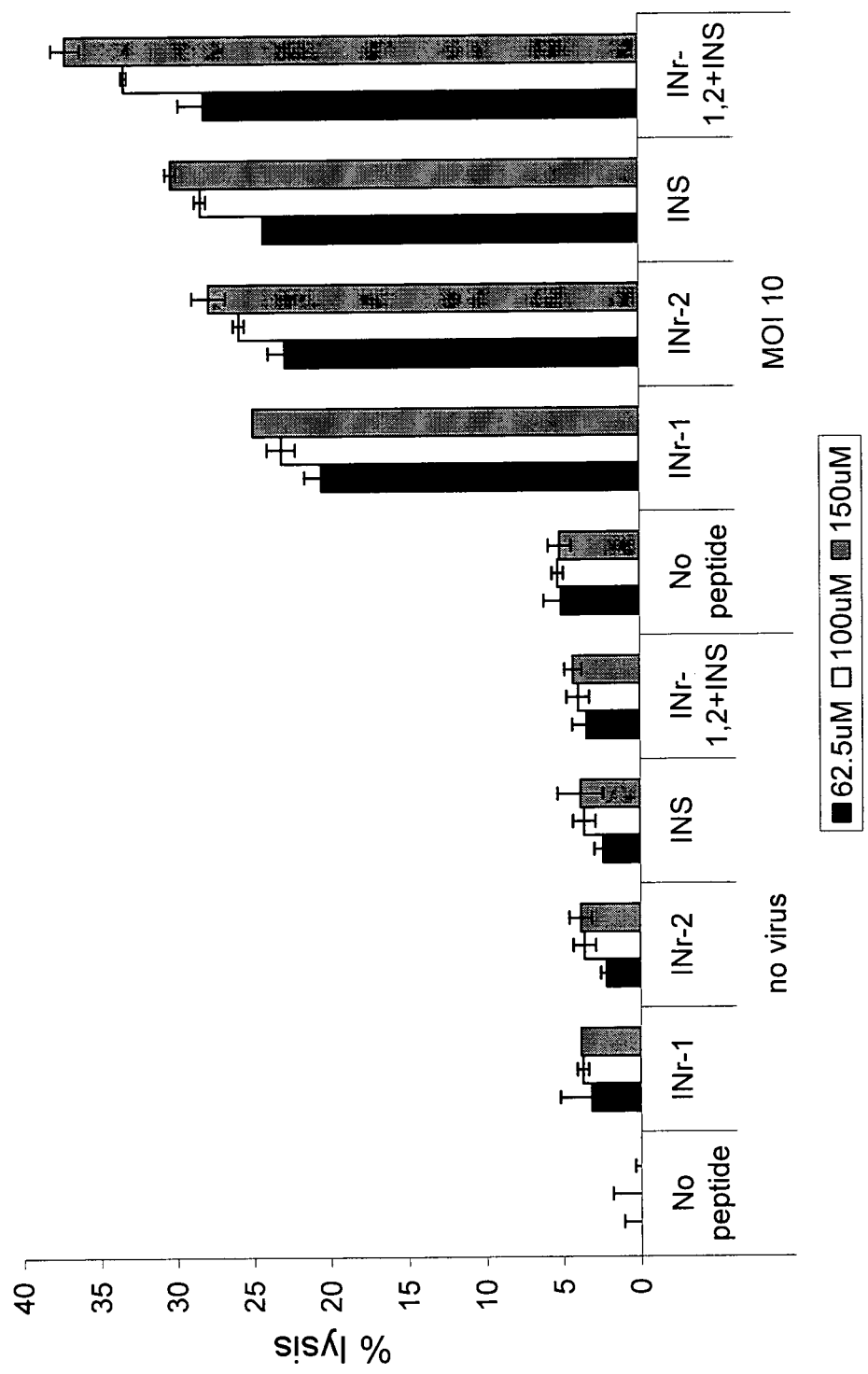
FIG. 8—induction of lysis of HIV-1 infected cells by the INS and INrs peptides. Cells were treated with INS or INrs peptides or a mixture of the three peptides and then infected with MOI 10 of ΔENV/VSV-G HIV-1 which promotes only one cycle of infection. Percentage lysis was measured by MTT 48 h post infection.

Promotion of Selective Cell Death by the INS and INrs Peptides in Virus Infected Cells but not in Control-Uninfected Cells The results in FIG. 7 show that the INS peptide induces lysis, namely cell death, of virus infected cells but not of control uninfected cells. As can be seen, only about 20-30% and about 100% intact viable infected and uninfected Hela cells respectively were left following incubation with 12.5 µM of the INS peptide. More then that, when determining the amount of cell death after one cycle of infection it can clearly bee seen that 62.5-150 µM INS and/or INrs induce killing of only infected lymphocyte cells. This effect is increased when a mixture of the peptides where added to the cells as shown in FIG. 8. Since one cycle of infection was used there is no production of new viruses therefore, killing of the cells is due to the multiple integration induced by the INS and the INrs peptides. These results clearly show that the INS and the INrs peptides cause selective death of virus infected cells thus can serve as a leader peptide to obtain small molecules which will selectively eliminate virus infected cells and thus function as anti HIV drug.

FIG. 7 Percentage of viable infected and uninfected Hela cells normalized every two days to the number of cells in the non treated non infected cells sample. Cells were infected with WT HIV-1 at MOI of 0.01 and the treated cells were added 12.5 µM of INS.

FIG. 8 Cells were treated with INS or INrs peptides or a mixture of all three peptide in the designated concentration then cells were infected with MOI 10 of ΔENV/VSV-G HIV-1 which promotes only one cycle of infection. MTT test was carried out 48 h post infection and the values were normalized to non-treated non-infected cells.

Example 5

A Combination of INrs+INS Peptides and the HIV-1 Specific Protease Inhibitor Ro 31-8959 Eradicate HIV-1

Figure 9A:
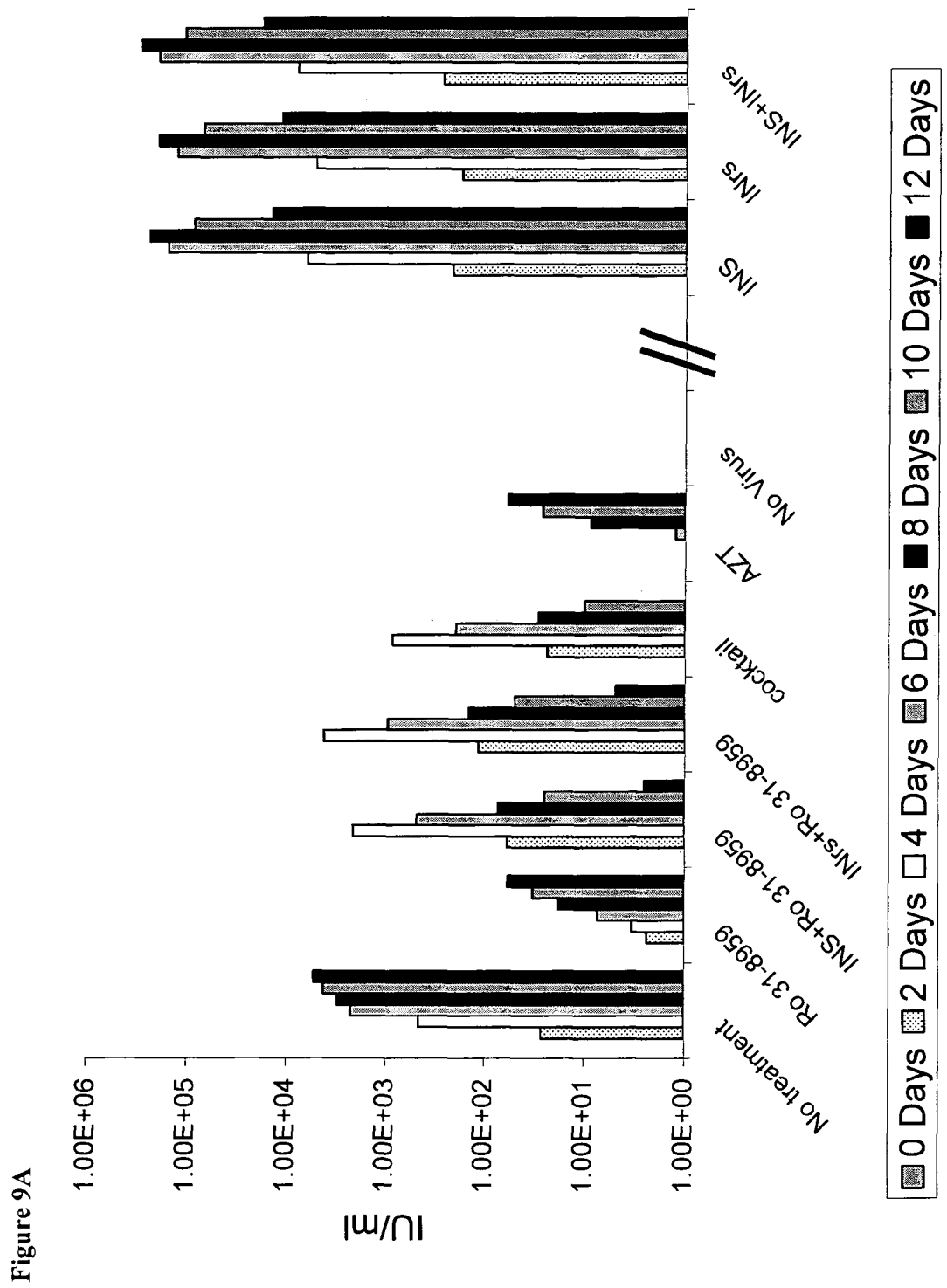
FIG. 9—eradication of HIV-1 from H9 cell following treatment with a combination of the INrs and INS peptides and the protease inhibitor Ro 31-8959. Cells were treated with peptides at 100 μM each, AZT at 2 μM and/or Ro31-8959 at 1 μM ("cocktail" represents a mixture or INS, INrs and Ro31-8959), and infected with MOI of 0.1 of wt HIV-1. Every 2 days the amount of infectious virus particles (A) and integration events per cell (B) were determined.
Figure 9B:
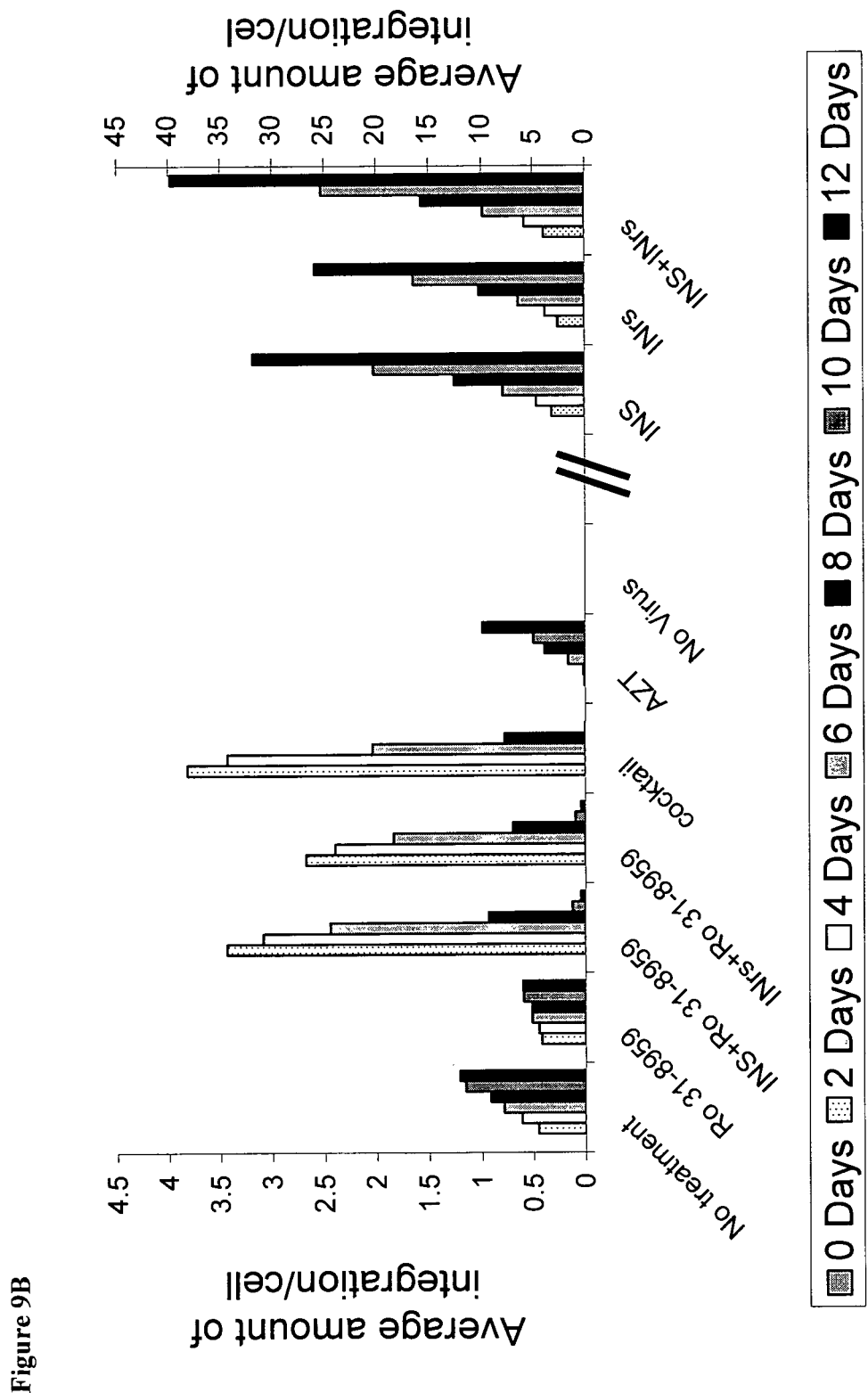

The results in FIG. 9 show that when H9 lymphocytes were treated with a combination of INr-1, INr-2 and INS and the HIV-1 protease inhibitor Ro 31-8959, no trace of virus integration or virus production could be detected after 12 days. It appears that this combination leads to a complete eradication of the virus.

FIG. 9 H9 cell were treated by the indicated compound (peptides at 100 µM each, AZT at 2 µM or Ro31-8959 at 1 µM. Cocktail represent a mixture or INS, INrs and Ro31-8959) and infected with MOI of 0.1 of wt HIV-1. Every 2 days the amount of infectious virus particles (A) and the amount of integration events per cell (B) were estimated as described above.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A synthetic or recombinant peptide selected from the group consisting of: WGSNFTSTTVKA (SEQ ID NO:5); WTAVQMAVFIHNFKRK (SEQ ID NO:6); and WTHLEGKIILVAVHVA (SEQ ID NO:7).

2. The peptide of claim 1, wherein the peptide further comprises a permeability-enhancing moiety comprising at least one aromatic amino acid residue.

3. A pharmaceutical composition comprising at least one peptide of claim 1.

4. The pharmaceutical composition of claim 3, comprising at least two different peptides.

5. The pharmaceutical composition of claim 3, further comprising another anti HIV-1 agent selected from the group consisting of: Danuravir, Saquinavir, Ritonavir, Indinavir, Nelfinavir, Amprenavir, Lopinavir, Atazanavir, Fosamprenavir, Tipranavir and Azidothymidine.

6. A method for treating HIV-1 infection or AIDS comprising administering to a subject in need thereof the pharmaceutical composition of claim 5.

* * * * *